US012004780B2

(12) United States Patent
Biedermann et al.

(10) Patent No.: US 12,004,780 B2
(45) Date of Patent: Jun. 11, 2024

(54) COUPLING DEVICE FOR COUPLING A ROD TO A BONE ANCHOR

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/505,939

(22) Filed: Oct. 20, 2021

(65) Prior Publication Data

US 2022/0125483 A1 Apr. 28, 2022

Related U.S. Application Data

(60) Provisional application No. 63/247,673, filed on Sep. 23, 2021, provisional application No. 63/104,133, filed on Oct. 22, 2020.

(30) Foreign Application Priority Data

Oct. 22, 2020 (EP) .................................... 20203461
Oct. 11, 2021 (EP) .................................... 21202039

(51) Int. Cl.
*A61B 17/70* (2006.01)
(52) U.S. Cl.
CPC ...... *A61B 17/7037* (2013.01); *A61B 17/7082* (2013.01)
(58) Field of Classification Search
CPC ............ A61B 17/7032; A61B 17/7035; A61B 17/7037; A61B 17/7038
See application file for complete search history.

(56) References Cited

U.S. PATENT DOCUMENTS 5,882,350 A 3/1999 Ralph et al.
6,248,105 B1 6/2001 Schläpfer et al.
(Continued)

FOREIGN PATENT DOCUMENTS

CN 2803295 Y 8/2006
CN 103976785 A 8/2014
(Continued)

OTHER PUBLICATIONS

Extended European Search Report for Application No. 20203461.7, dated Apr. 28, 2021, 11 pages.
(Continued)

*Primary Examiner* — Julianna N Harvey
*Assistant Examiner* — Anna V. Little
(74) *Attorney, Agent, or Firm* — Lewis Roca Rothgerber Christie LLP

(57) ABSTRACT

A coupling device for coupling a rod to a bone anchor includes a receiving part having first and second ends, a central axis, and two legs defining a recess at the first end for receiving the rod, a pressure member configured to exert pressure on an inserted head, and an actuating member with an engagement surface configured to engage the pressure member. When a first portion of the actuating member moves axially in a first direction, the engagement surface is configured to move from a first axial position to a second axial position to adjust the pressure member from a non-locking position where the head is pivotable to a locking position where the head is locked. When a second portion of the actuating member moves in the first direction, the pressure member is adjusted from the locking position back to the non-locking position.

29 Claims, 28 Drawing Sheets

(56) References Cited

U.S. PATENT DOCUMENTS

| | | |
|---|---|---|
| 8,506,609 B2 | 8/2013 | Biedermann et al. |
| 8,556,938 B2 | 10/2013 | Jackson et al. |
| 8,888,827 B2 | 11/2014 | Harper et al. |
| 8,926,671 B2 | 1/2015 | Biedermann et al. |
| 8,951,294 B2 | 2/2015 | Gennari et al. |
| 9,155,567 B2 | 10/2015 | Auerbach et al. |
| 9,839,446 B2 | 12/2017 | Biedermann et al. |
| 10,271,877 B2 | 4/2019 | Biedermann et al. |
| 2006/0264933 A1* | 11/2006 | Baker ................ A61B 17/7037 606/328 |
| 2007/0167949 A1 | 7/2007 | Altarac et al. |
| 2009/0030457 A1* | 1/2009 | Janowski ........... A61B 17/7037 606/301 |
| 2010/0152787 A1 | 6/2010 | Walsh et al. |
| 2010/0234902 A1 | 9/2010 | Biedermann et al. |
| 2011/0112578 A1* | 5/2011 | Keiser ................ A61B 17/7032 606/264 |
| 2012/0046701 A1 | 2/2012 | Gennari et al. |
| 2013/0096622 A1 | 4/2013 | Biedermann et al. |
| 2013/0096623 A1 | 4/2013 | Biedermann et al. |
| 2014/0188173 A1 | 7/2014 | Mishra et al. |
| 2014/0236239 A1 | 8/2014 | Biedermann et al. |
| 2014/0257411 A1 | 9/2014 | Rezach |
| 2015/0080960 A1 | 3/2015 | Biedermann et al. |
| 2017/0172630 A1* | 6/2017 | Biedermann ...... A61B 17/7002 |
| 2019/0209214 A1* | 7/2019 | Biedermann ...... A61B 17/7034 |
| 2019/0223917 A1* | 7/2019 | Gray ................. A61B 17/7082 |
| 2019/0262044 A1* | 8/2019 | Roth .................... A61B 17/70 |

FOREIGN PATENT DOCUMENTS

| | | |
|---|---|---|
| CN | 104434283 A | 3/2015 |
| EP | 2 851 021 A1 | 3/2015 |
| WO | WO 2015/059590 A1 | 4/2015 |

OTHER PUBLICATIONS

European Search Report dated Nov. 17, 2015 for Application No. 15167435.5; (7 Pages).

* cited by examiner

COUPLING DEVICE FOR COUPLING A ROD TO A BONE ANCHOR

CROSS-REFERENCE TO RELATED APPLICATION(S)

The present application claims priority to and the benefit of U.S. Provisional Patent Application No. 63/247,673, filed Sep. 23, 2021, and U.S. Provisional Patent Application No. 63/104,133, filed Oct. 22, 2020, the contents of which are hereby incorporated by reference in their entirety, and claims priority from European Patent Application EP 21 202 039.0 filed Oct. 11, 2021 and European Patent Application EP 20 203 461.7, filed Oct. 22, 2020, the contents of which are hereby incorporated by reference in their entirety.

BACKGROUND

Field

The application relates to a coupling device for coupling a rod to a bone anchor, and in particular relates to a polyaxial bone anchoring device that permits locking of a polyaxial position of the bone anchor independently of the rod.

Description of Related Art

A polyaxial bone anchoring device of this type is known, for example, from U.S. Pat. No. 9,155,567 B2. The polyaxial pedicle screw described in this document includes a receiving head having a transversal U-shaped passage, and a shank having a threaded portion and a bulging end rotatable housed within the receiving head. A locking insert is also housed within the receiving head and is matable with the bulging end. The receiving head includes a lateral aperture, the lateral aperture exposing a contact surface of the locking insert in such a way that an external pressing component can act on the contact surface to maintain the locking insert into its locking position.

In US 2019/0209214 A1, a polyaxial bone anchoring device is described that includes a receiving part with two legs defining a recess for receiving a rod, and a pressure member for exerting pressure on a head of the bone anchor in the receiving part. The pressure member has an engagement portion that extends at least partially into a leg of the receiving part and is directly engageable from outside the bone anchoring device. With an instrument, for example, the pressure member can be adjusted from a non-locking position where the head is pivotable to a locking position where the head is clamped.

SUMMARY

In spinal surgery, often multiple segments of the spinal column have to be corrected and/or stabilized using a spinal rod and polyaxial bone anchors. During such a procedure, repeated adjustments of the bone anchor and the rod relative to a receiving part of a polyaxial bone anchoring device may become necessary. Therefore, there is a need for simple and effective handling of the polyaxial bone anchoring device in terms of locking and unlocking of the head and the rod during correction steps.

It is an object of the invention to provide an improved coupling device and an improved poly-axial bone anchoring device, as well as a system including such a coupling device or such a polyaxial bone anchoring device and an instrument that is convenient to operate and/or effective in terms of locking.

According to an embodiment, a coupling device for coupling a rod to a bone anchor includes a receiving part configured to receive a head of the bone anchor, the receiving part having a first end and a second end, a central axis extending through the first end and the second end, and two legs defining a recess at the first end for receiving the rod. The coupling device further includes a pressure member movable in the receiving part to exert pressure on an inserted head. An actuating portion configured to act on the pressure member is provided on the receiving part. The actuating portion is configured to rotate at least partially around an axis of rotation that extends at an angle or is inclined relative to the central axis to move the pressure member from a non-locking position in which an inserted head is pivotable in the receiving part to a locking position in which the head is clamped. Preferably the axis of rotation is substantially perpendicular to the central axis so that the pressure member is moved downward towards the second end. Further preferably the actuating portion includes a cam portion and the pressure member follows the movement of the cam portion.

With such a structure, a rotational movement of the actuating portion can be transformed into a linear movement of the pressure member. This permits movement of the pressure member only a small distance for locking the head. More specifically, the actuating portion may include a rotating shaft and a cam portion that acts on the pressure member. This permits to precisely effect a small movement of the pressure member with a simple construction.

The locking of the head may be temporary as long as the instrument acts on the actuating portion. Hence, the steps of adjusting the angular position of the coupling device relative to the bone anchor can be carried out repeatedly in a quick and easy manner.

According to an embodiment, the actuating portion is rotatable in a first direction to move the pressure member to the locking position and in a second direction, preferably opposite to the first direction, to move the pressure member to the non locking position.

According to an embodiment, the actuating portion is configured to cooperate with the receiving part in a non-threaded manner. According to a further embodiment, the actuating portion is substantially stationary in a direction of the axis of rotation while rotating. According to a still further embodiment, the actuating portion is configured to rotate when a force in the direction of the central axis is applied thereto. According to a still further embodiment, the axis of rotation intersects the central axis.

An embodiment of an instrument includes a first instrument portion, preferably an outer tube, the first instrument portion being configured to engage the receiving part, a second instrument portion, preferably an inner portion arranged at least partially in the first instrument portion and being displaceable relative to the first instrument portion, the second instrument portion being configured to engage the actuating portion. When the first instrument portion engages the receiving part and the second instrument portion engages the actuating portion and rotates the actuating portion, the pressure member is movable from a non-locking position in which an inserted head is pivotable in the receiving part to a locking position in which the head is clamped. In a still further embodiment the second instrument portion is configured to rotate the actuating portion in an opposite direction so that the pressure member is moved from the locking position back to the non locking position.

According to a further embodiment, the instrument includes a first instrument portion that is configured to be attached to the receiving part and a second instrument portion that is configured to act on the actuating portion of the receiving part to rotate the actuating portion in a first direction to move the pressure member to the locking position and to actuate the actuating portion in a second direction, preferably opposite to the first direction, to move the pressure member to the non locking position. The actuating portion of the receiving part may include a two-armed lever, the pivot axis of which coincides with the axis of rotation of the actuating portion. The second instrument portion may include a first pushing member that is configured to act on one arm of the two-armed lever and a second pushing member that is configured to act on the other arm of the two-armed lever. Since the receiving part may have two actuating portions, a pair of pushing members may be provided for each actuating portion. With this embodiment the head can be selectively locked and unlocked with respect to the receiving part.

The instrument may be designed such that the recess of the receiving part that receives the rod can remain unobstructed during the locking of the head of the bone anchor. Hence, it is possible to temporarily lock the head of the bone anchor while a rod and/or a fixation member is not yet placed in the rod channel, or in the case that the rod is at a higher position than the bottom of the rod channel. This may increase possibilities for surgical correction steps.

The bone anchoring device may be a bottom loading bone anchoring device, where the head of the bone anchor is insertable from the lower end of the receiving part, or a top loading bone anchoring device where the bone anchor is insertable into the receiving part from the upper end.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
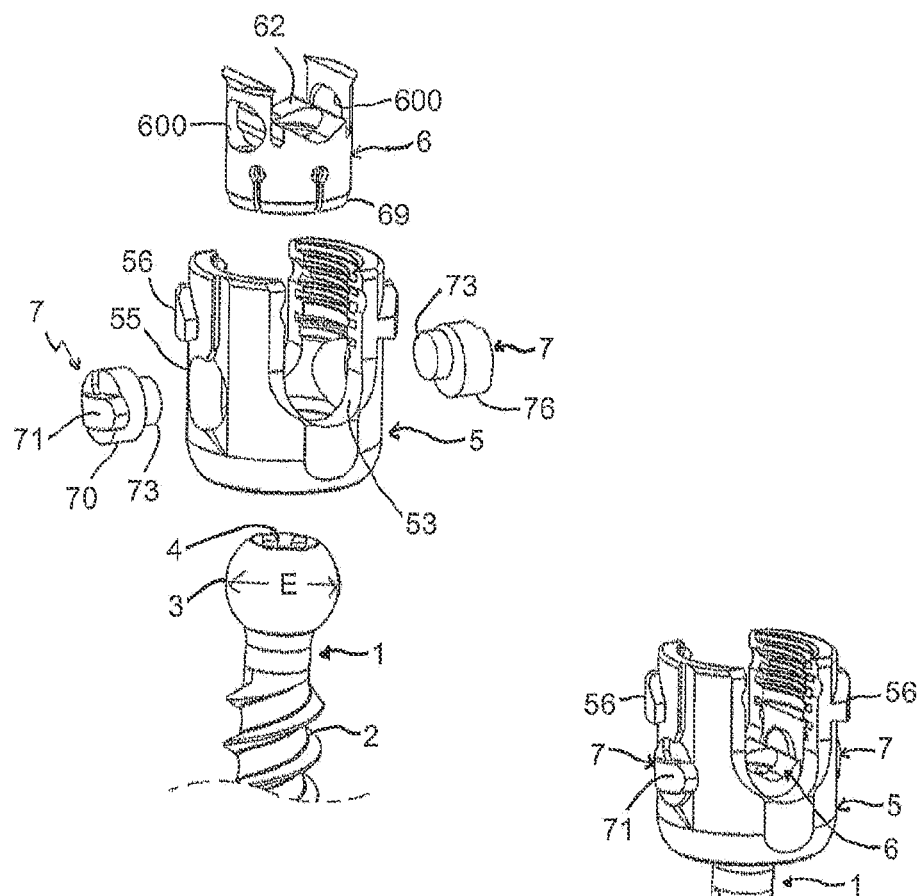
FIG. 1 shows an exploded perspective view of a first embodiment of a polyaxial bone anchoring device that includes a coupling device.
Figure 2:
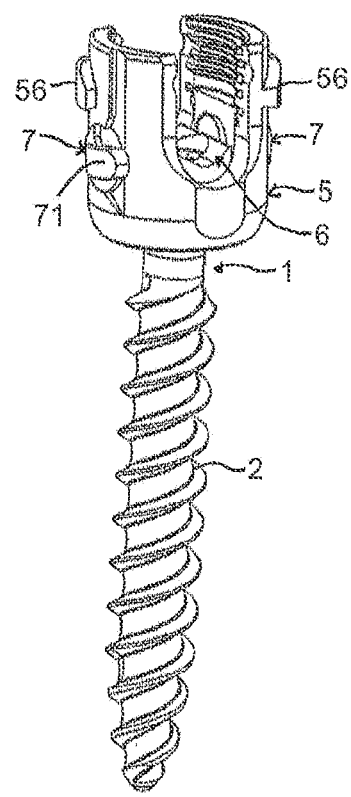
FIG. 2 shows a perspective view of the polyaxial bone anchoring device of FIG. 1 in an assembled state.
Figure 3:
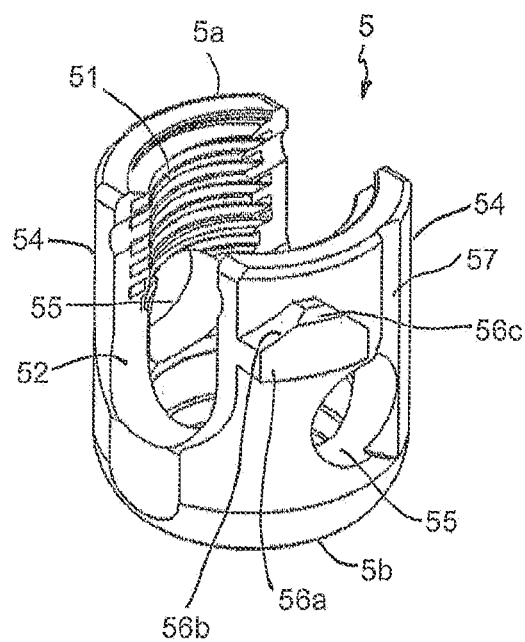
FIG. 3 shows a perspective view from a top of a receiving part of the polyaxial bone anchoring device of FIGS. 1 and 2.
Figure 4:
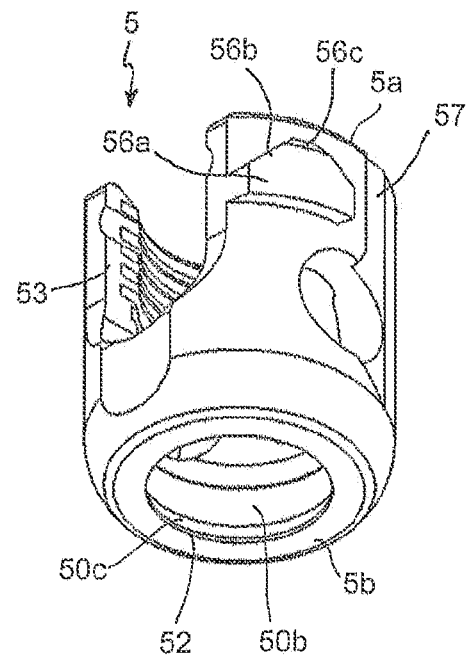
FIG. 4 shows a perspective view from a bottom of the receiving part of FIG. 3.
Figure 5:
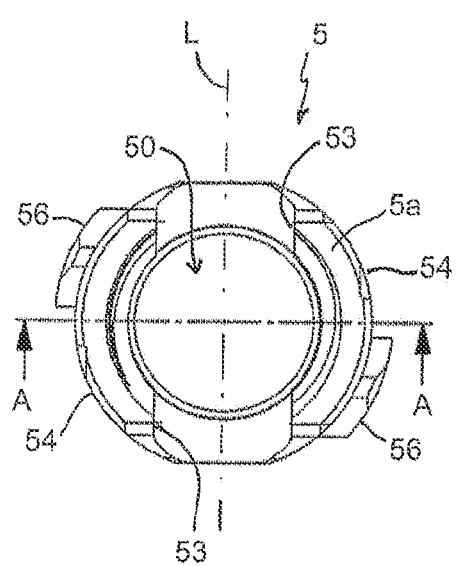
FIG. 5 shows a top view of the receiving part of FIGS. 3 and 4.
Figure 6:
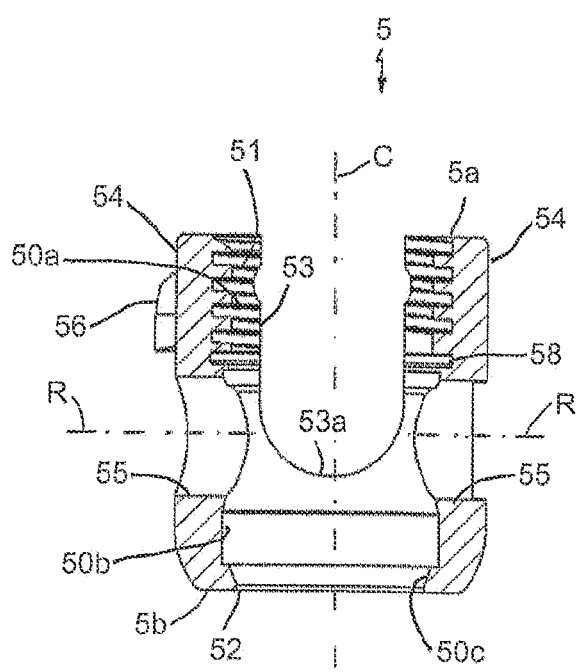
FIG. 6 shows a cross-sectional view of the receiving part of FIGS. 3 to 5, the cross-section taken along line A-A in FIG. 5.
Figure 7:
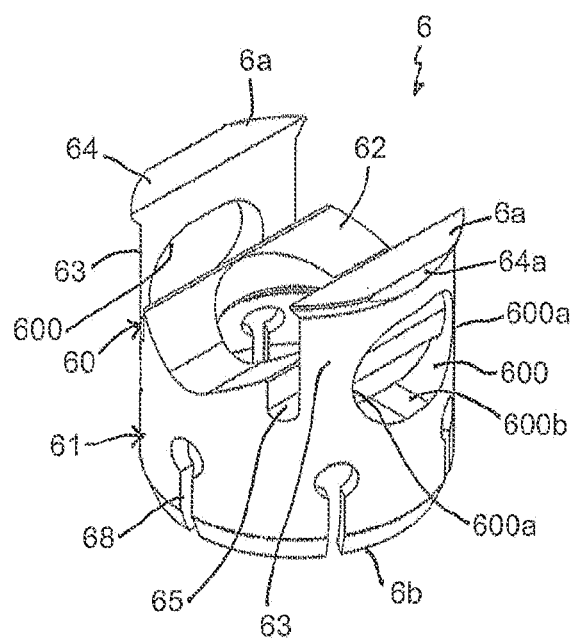
FIG. 7 shows a perspective view from a top of a pressure member of the polyaxial bone anchoring device of FIGS. 1 and 2.
Figure 8:
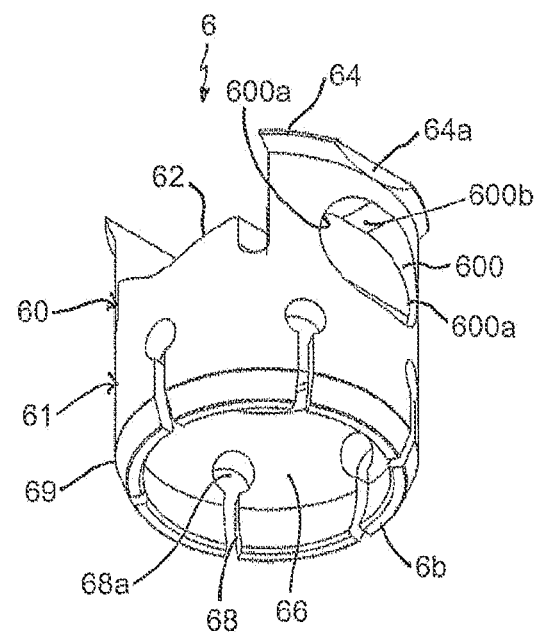
FIG. 8 shows a perspective view from a bottom of the pressure member of FIG. 7.
Figure 9:
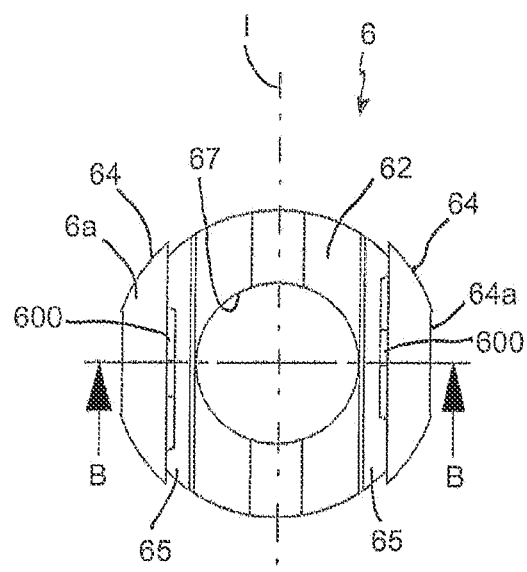
FIG. 9 shows a top view of the pressure member of FIGS. 7 and 8.
Figure 10:
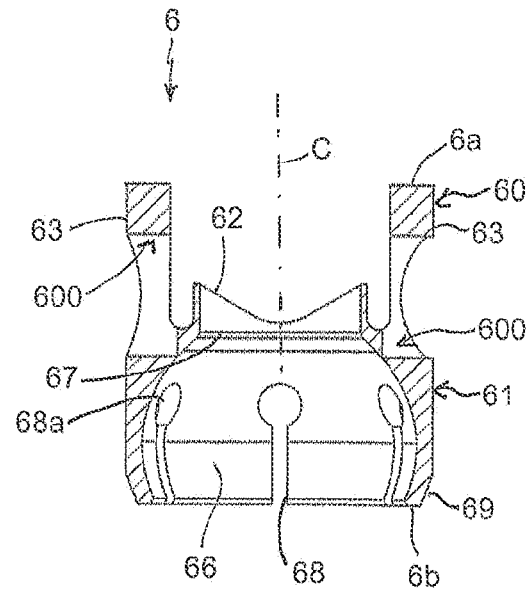
FIG. 10 shows a cross-sectional view of the pressure member of FIGS. 7 to 9, the cross-section taken along line B-B in FIG. 9.

As depicted in FIGS. 1 and 2, a bone anchoring device according to an embodiment of the invention includes a bone anchor 1 in the form of, for example, a bone screw having a shank 2 with a threaded portion and a head 3 with a spherically-shaped outer surface portion. The head 3 may also have a recess 4 for engagement with a drive tool. The bone anchoring device also includes a coupling device that includes a receiving part 5 for receiving a rod (not shown) to be connected to the bone anchor 1. In addition, a pressure member 6 forms a part of the coupling device. The pressure member 6 is provided in the receiving part 5 and is configured to exert pressure on the head 3 of the bone anchor 1 to clamp and/or finally lock the head 3 with respect to the receiving part 5. Two actuating members 7 that generally form actuating portions are mounted in opposite walls of the receiving part 5 and are configured to actuate the pressure member 6 to exert pressure on the head 3. The bone anchoring device may further include a fixation member (not shown), for example, an inner screw or set screw, for fixing the rod in the receiving part 5.

The receiving part 5 will be described in greater detail, referring additionally to FIGS. 3 to 6. The receiving part 5 includes a first end 5a forming an upper end and an opposite second end 5b forming a lower end, and a central axis C that passes through the first end 5a and the second end 5b. The overall outer shape of the receiving part may be substantially cylindrical, except for structures such as projections and/or grooves that are formed on or in the cylindrical surface. A passage 50 extends through the receiving part 5 from the first end 5a to the second end 5b. The passage 50 may have several sections having different diameters. In one section that starts at or close to the first end 5a and extends to a distance from the first end 5a, the passage 50 is formed as a first coaxial bore 50a that may be provided in at least a portion thereof with an internal thread 51. Between the first coaxial bore 50a and the second end 5b, a widened portion in a form of a second coaxial bore 50b may be provided that permits a portion of the pressure member 6 to expand therein. Between the second end 5b and the second coaxial bore 50b, a narrowing portion 50c is formed that narrows, for example in a conical shape, towards the second end 5b. By the passage 50, an opening 52 is formed at the second end 5b, a width of which is greater than a greatest outer diameter E of the head 3. Hence, the receiving part 5 is suitable for insertion of the head 3 of the bone anchor 1 through the opening 52 at the second 5b into the receiving part 5.

In a region adjacent to the first end 5a of the receiving part 5, a recess 53 that may be substantially U-shaped extends from the first end 5a in the direction of the second end 5b. A width of the recess 53 is slightly greater than a diameter of the rod to be inserted, such that the rod can be placed in the recess 53 and can be guided therein. By means of this, the recess 53 forms a rod receiving recess or a channel for the rod, wherein sidewalls of the channel define two free legs 54. Each of the legs 54 has a transverse hole 55. The transverse holes 55 extend completely from the outer surface of the receiving part 5 into the passage 50, and may be substantially cylindrical holes having a cylinder axis R. In the embodiment, the cylinder axis R extends perpendicular to the central axis C and intersects the central axis C. The holes 55 may extend to an axial height slightly above a bottom 53a of the substantially U-shaped recess 53. Moreover, the cylinder axis R of the holes 55 may extend substantially through a center of the legs 54 in the circumferential direction. Hence, the holes are substantially symmetrical with respect to a plane extending through the central axis C and through a center of the legs 54, and the cylinder axes R of the two holes 55 are coincident. An inner diameter of the holes 55 is only slightly greater than an outer diameter of the actuating members 7, such that the actuating members 7 can be inserted in the holes 55, respectively, and are rotatably supported therein. Hence, the cooperation between the actuating members 7 and the receiving part is non-threaded.

On each leg 54, above the hole 55, a protrusion 56 formed on the outer wall of the leg 54 serves as an engagement portion for engaging the receiving part 5 with an instrument. The protrusions 56 are asymmetrical with respect to each other in relation to a plane extending through the central axis and the center of each leg. In greater detail, each protrusion 56 is offset from the hole 55 in the same circumferential direction and adjoins the border of the recess 53. As can be seen in particular in the top view of FIG. 5, one protrusion 56 at one leg 54 which is on one side of the longitudinal axis of the recess 53 is offset towards one border of the recess 53 in the direction of the axis L. The other protrusion 56 at the other leg 54 is on the opposite side of the longitudinal axis L of the recess 53 and is offset towards an opposite border of the recess 53 in the direction of the axis L. The protrusion 56 has a four-cornered base 56a with a cylindrical outer surface and a roof-shaped portion 56b that is oriented towards the first end 5a. The roof-shaped portion 56b may have a beveled portion 56c at its tip region. In the example shown, the protrusion 56 is on one side flush with the border of the recess 53. It shall be noted that the protrusion may have other shapes that render it suitable for engagement with an instrument.

In addition, the receiving part 5 has on each leg 54 a groove 57 in its outer wall for guiding a portion of an instrument to the actuating member 7 when the actuating member 7 is placed into the hole 55. The groove 57 extends substantially parallel to the central axis C from the first end 5a to a distance from the second end 5b and is located adjacent to the hole 55 on a side opposite to the protrusion 56 in the circumferential direction. Moreover, the groove 57 may be open towards the hole 55. At a distance from the lowermost end of the internal thread 57, a circumferentially extending groove 58 may be formed in the inner wall of the receiving part that serves as an abutment for a portion of the pressure member 6.

Referring additionally to FIGS. 7 to 10, the pressure member 6 will be described in greater detail. The pressure member 6 includes a first end 6a that forms an upper end and a second end 6b that forms a lower end. An upper portion 60 of the pressure member includes a rod receiving portion and a lower portion 61 of the pressure member includes a head receiving portion. The outer surface of the pressure member 6 is substantially cylindrical with an outer diameter such that the pressure member 6 can be placed into the passage and can slide in the coaxial bore 50a of the receiving part 5. When the pressure member 6 is mounted to the receiving part 5, the central axis of the pressure member coincides with the central axis C of the receiving part. In the upper portion 60, a rod support surface 62 may be provided that is configured to support an inserted rod. A longitudinal axis I of the rod support surface 62 extends transverse to the central axis C. The rod support surface 62 may have a V-shaped cross-section when viewed in a direction transverse to the central axis C, to permit support of rods of different diameters. However, the rod support surface can also be flat or cylindrical or can have any other shape. To the left and to the right of the rod support surface 62, upstanding legs 63 are formed that have a substantially flat inner surface and a substantially cylindrical outer surface.

Adjacent to the first end 6a, a substantially cylindrical rim portion 64 is formed on each leg 63 that protrudes beyond the outer surface of the cylindrical main portion 60 of the pressure member 6. An outermost section of the rim portion 64 may be cut away so that a flattened outer end 64a may be formed. At the center of the legs 63 in the circumferential direction the flattened end 64a may be flush with the cylindrical outer surface of the pressure member. The rim portion 64 is configured to engage the groove 58 of the receiving part 5, to prevent the escape of the pressure member 6 through the first end once the pressure member has been placed into the receiving part 5 and assumes an insertion position for the head 3. Between the rod support surface 62 and the upstanding legs 63, grooves 65 extending parallel to the rod support surface 62 are formed that render the upstanding legs 63 slightly more flexible.

In the lower portion 61 of the pressure member 6, a head receiving recess 66 is provided for the head 3 of the bone anchor 1. The head receiving recess 66 may be substantially spherically-shaped with a radius corresponding to that of the head 3, and extends over the region of the head with the greatest outer diameter E. The lower portion also has a plurality of slits 68 that are open at the second end 6b. The number and dimensions of the slits 68 are such that the wall confining the head receiving recess 66 is flexible, and more specifically, that the wall can expand to snap onto the head 3 when the head 3 is inserted. To increase the flexibility, the closed end portions 68a of the slits 68 may be widened. An outer surface portion 69 adjacent to the second end 6b of the pressure member 6 may be tapered, for example, conically tapered. The outer surface portion 69 is configured to cooperate with the narrowing portion 50c of the passage of the receiving part 5. A coaxial bore 67 in the pressure member 6 permits access to the head 3 with a drive tool.

In each of the legs 63, a recess 600 is formed that extends completely through the leg laterally from outside to inside. The recesses 600 are elongate in the circumferential direction and have substantially cylinder segment-shaped ends 600*a*, connected by two substantially straight portions 600*b*. Moreover, the recesses 600 have a length in the circumferential direction and a height in the axial direction of the central axis C, such that a protrusion of the actuating member 7 is configured to move therein substantially only in the lengthwise direction of the elongate hole 600. More specifically, the recesses 600 are arranged asymmetrical with respect to the center of the legs in the circumferential direction, as can be seen in particular in FIGS. 9 and 10. One recess 600 on one leg 63 is offset from the center of the leg towards one side, and the other recess 600 is offset from the center of the other leg 63 towards the opposite side. This follows from the eccentric arrangement of the engagement portions on the actuating members 7, as explained below.

Figure 11:
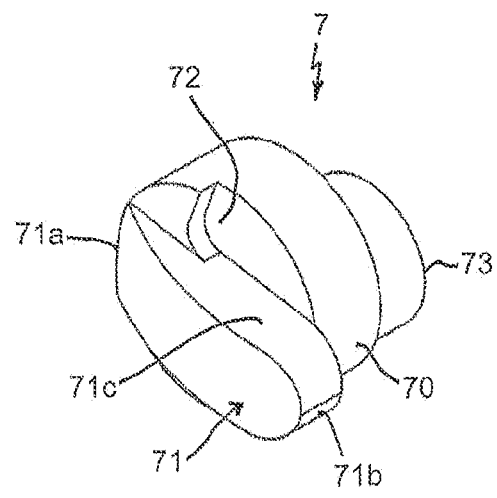
FIG. 11 shows a perspective view from a top of an actuating portion in the form of an insert member of the polyaxial bone anchoring device of FIGS. 1 and 2.
Figure 12:
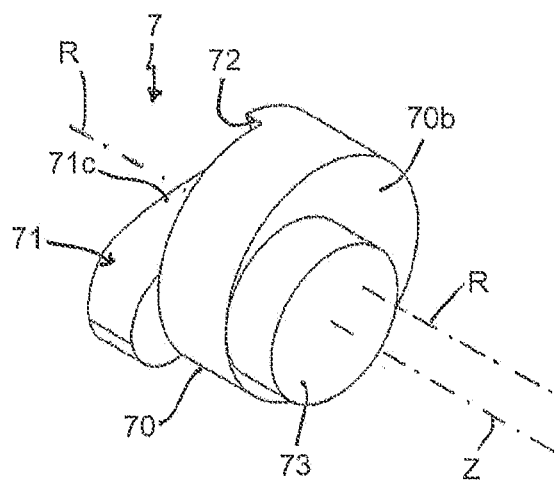
FIG. 12 shows a perspective view from a bottom of the actuating portion of FIG. 11.
Figure 13:
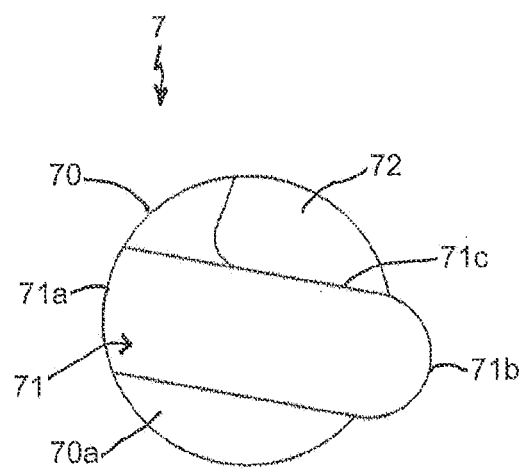
FIG. 13 shows a side view of the actuating portion of FIGS. 11 and 12.

As shown in FIGS. 1 and 2 and additionally in FIGS. 11 to 13, the actuating members 7 may be identical and may each be designed as a monolithic piece that is insertable into a hole 55 of the receiving part 5. More specifically, each actuating member 7 has a cylindrical main portion 70 that has an outer diameter such that the actuating member can be placed into the hole 55 in the leg 54 of the receiving part 5 and is rotatably supported in the hole 55. The main portion 70 includes two opposite circular or partially circular end faces, one of which forms an outside face 70*a* which faces to the outside of the receiving part 5, and the opposite one forms an inside face 70*b* which faces to the inside of the receiving part 5, when the actuating member is mounted to the receiving part 5. The thickness of the main portion 70 substantially corresponds to the wall thickness of the receiving part around the holes 55.

On the outside face 70*a*, a lever-like protrusion 71 that has a rear end 71*a* and an opposite free forward end 71*b* is formed. The lever-like protrusion 71 has a thickness perpendicular to the outside face that may smoothly increase from the rear end 71*a* to a distance from the rear end 71*a*, and may then be constant up to the free end 71*b*. The free end 71*b* may protrude beyond the contour of the outside surface 70*a*. As shown in particular in FIG. 13, the position of the lever-like protrusion 71 may be such that the protrusion extends over the region with the largest diameter of the outside surface 70*a* but may be arranged closer to one side of the main portion 70 than to an opposite side in a direction perpendicular to the lever axis. An upper side 71*c* of the lever-like protrusion 71 forms an engagement surface that is configured to be engaged by a portion of the instrument. Adjacent to the engagement surface 71*c*, the outside surface 70*a* has a recess 72 where a portion of the main body 70 is cut away. The recess 72 may provide guidance and space for a portion of the instrument.

When the actuating member 7 is inserted into the hole 55, the cylinder axis of the main portion 70 is coincident with the cylinder axis R of the hole and forms an axis of rotation R for the actuating member 7. At the inside surface 70*b*, an engagement portion for engaging the pressure member in the form of a cylindrical protrusion 73 is provided that has an outer diameter smaller than an outer diameter of the main portion 70 of the actuating member 7. The cylindrical protrusion 73 is at the inside face 70*b* at a position opposite to the front region of the lever-like protrusion 71 and may extend up to the outer edge of the main portion 70. The cylinder axis z of the cylindrical protrusion 73 extends parallel to the cylinder axis R of the main portion 70, hence the cylinder axis z of the cylindrical protrusion 73 is offset from the axis of rotation R of the main portion 70. By means of this, the cylindrical protrusion 73 serves as an eccentric actuating portion, more specifically as a cam portion. The height of the cylindrical protrusion 73 is such that once the actuating member 7 is mounted in the hole 55, the cylindrical protrusion 73 extends into the recess 600 of the leg 63 of the pressure member 6. As a result, when the lever-like protrusion 71 is engaged by an instrument and pressed down, the actuating member 7 is rotated to some extent in the hole 55. While rotating, the actuating member 7 may be stationary in the direction of the axis of rotation. The cylindrical protrusion 73 is confined in its movement in the recess 600 between the ends 600*a*. As the cylindrical protrusion 73 moves on an eccentric path around the axis of rotation R, the protrusion moves downward and the pressure member 6 follows this movement, thereby exerting a downwardly directed force onto an inserted head 3. Hence, the cylindrical protrusion acts as a cam.

Figure 14:
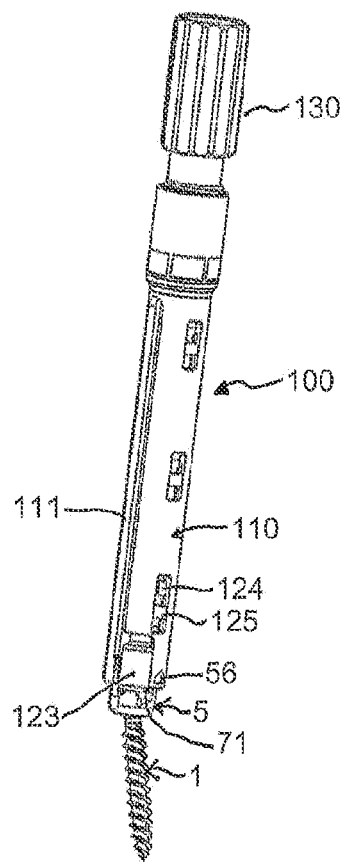
FIG. 14 shows a perspective view of a system including the polyaxial bone anchoring device of FIGS. 1 and 2 and an instrument attached thereto.
Figure 15:
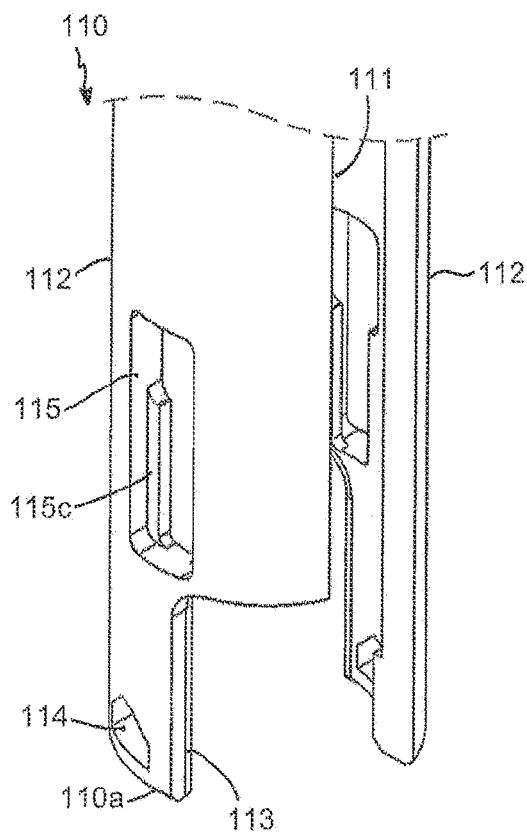
FIG. 15 shows a perspective view from a top of a front portion of an outer member of the instrument of FIG. 14.
Figure 16:
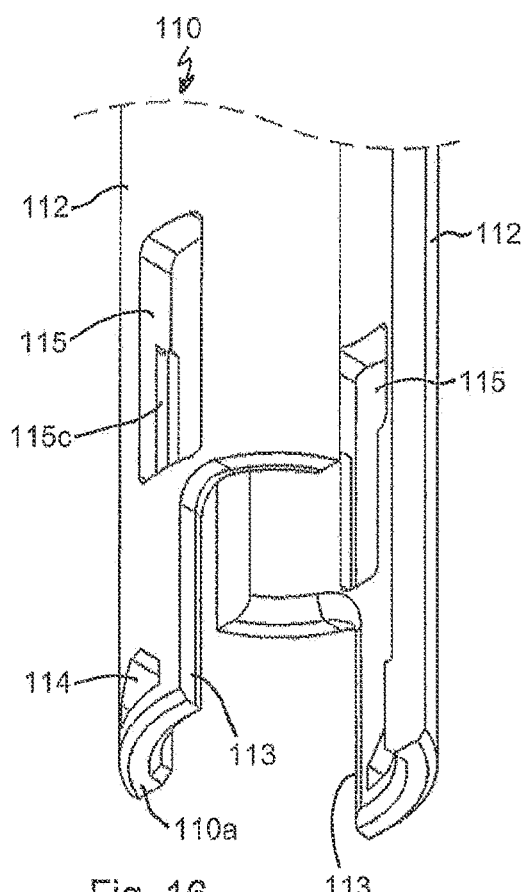
FIG. 16 shows a perspective view from a bottom of the front portion of FIG. 15.
Figure 17:
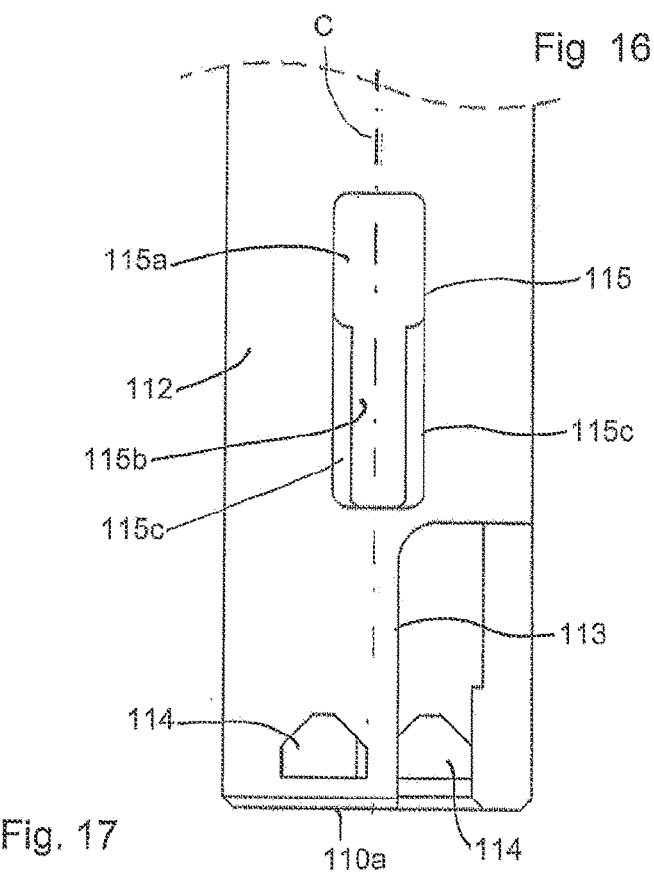
FIG. 17 shows a side view of the front portion of FIGS. 15 and 16.

Referring now to FIGS. 14 to 20, an instrument which is suitable for use with the bone anchoring device described above will be explained. The instrument 100 includes a first instrument portion in the form of an outer member 110 and an inner member 120. The inner member 120 is displaceable relative to the outer member 110, and a handle and/or actuating device including, for example, a rotating knob 130 is provided for displacing the inner member relative to the outer member. Various mechanisms may be implemented to displace the inner member 120 relative to the outer member 110. An overall shape of each of the inner and outer members is tubular, although the tubes may have slits so that the tubes are not completely closed. A central longitudinal axis of the tube coincides with the central longitudinal axis C of the receiving part when the instrument is attached thereto. Referring in addition to FIGS. 15 to 17, a front portion of the outer member 110 is shown in an enlarged view. The outer member 110 has a front end 110*a* that in use faces towards the bone anchoring device. Two opposite slits 111 that are open at the front end 110*a* extend over a portion of the outer member, so that two arms 112 are formed that are flexible at least to an extent such that the arms can spread apart to engage the protrusions 56 at the receiving part 5. The width of the longitudinal slits 111 may be at least as large as the diameter of the rod to be inserted into the receiving part. This permits use of the instrument when a rod is already inserted in the receiving part or when the rod has to be inserted when the instrument is attached to the receiving part.

Furthermore, a substantially rectangular cutout 113 is formed on each of the arms 112 adjacent to the recess 111 and to the front 110*a*. The width of the recesses 113 in the circumferential direction is such that a portion of the inner member 120 can extend therein. Moreover, the cut-outs 113 are at positions that are asymmetric with respect to the substantially U-shaped recess 53 of the receiving part 5 when the instrument is attached thereto. Specifically, the cutouts 113 are provided at different sides of the U-shaped recess 53 and at different ends of the U-shaped recess 53 in the direction of longitudinal axis L of the U-shaped recess 53. Furthermore, at a distance from the front end 110*a*, an engagement recess 114 is provided on each arm 112. The engagement recess 114 is located on each arm 112 at a position for engaging the protrusion 56 on the receiving part 5 when the outer member 110 is placed onto the receiving part 5. Moreover, the contour of the engagement recesses 114 substantially matches the contour of the engagement protrusions, so that a form-fit engagement can be achieved.

At substantially a center of each of the arms 112 in the circumferential direction, an axially elongate guiding recess 115 is formed that is sized and shaped to provide guidance for protrusions of the inner member 120. In greater detail, each recess 115 has an upper region 115a and a lower region 115b that is narrowed with respect to the upper region 115a. This is achieved by two wings 115c that extend from the longitudinal sides of the recess 115 towards the middle in the circumferential direction. The wings 115c are positioned at a distance from the outer surface of the front portion 110 so that, as depicted in FIG. 14, a portion of the inner member 120 that extends between the wings 115c is still within the recess 115, or in other words does not protrude substantially to the outside.

Figure 18:
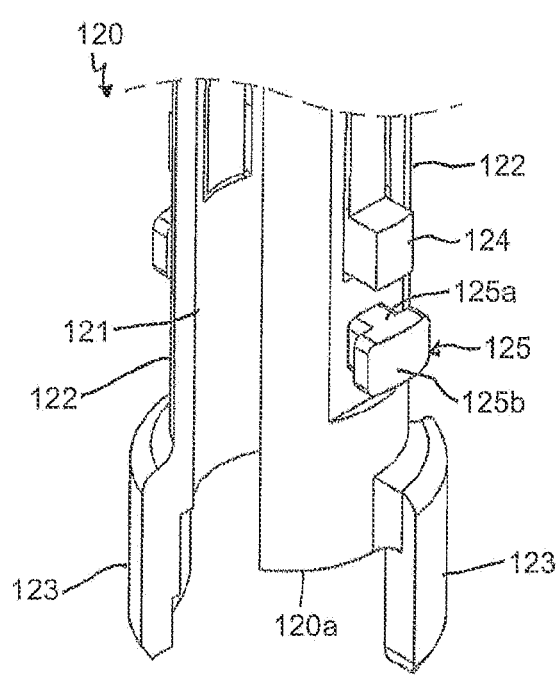
FIG. 18 shows a perspective view from a top of a front portion of an inner member of the instrument of FIG. 14.
Figure 19:
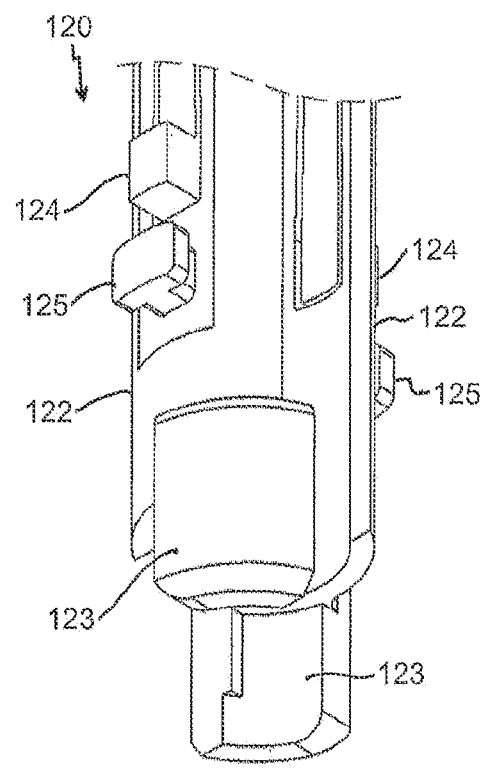
FIG. 19 shows a perspective view from a bottom of the front portion of the inner member of FIG. 18.
Figure 20:
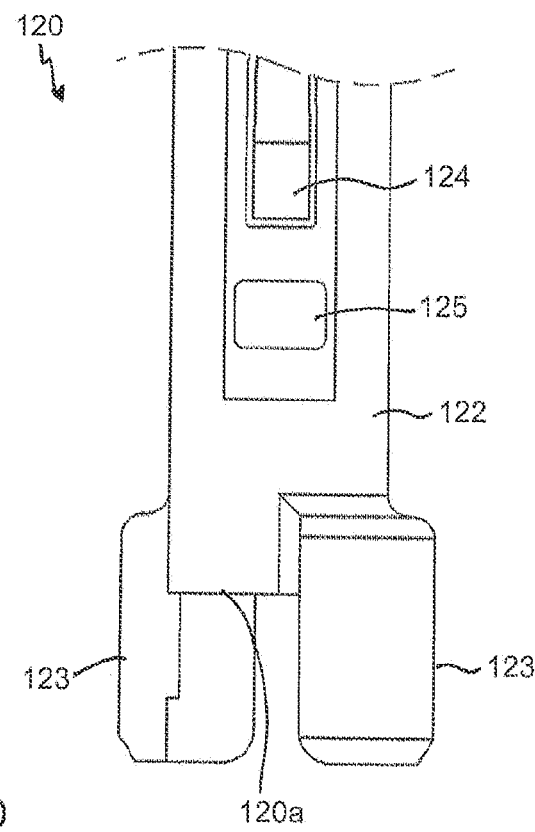
FIG. 20 shows a side view of the front portion of the inner member of FIGS. 18 and 19.

A front portion of the inner member 120 is illustrated in greater detail in FIGS. 18 to 20. The inner member 120 has an outer diameter that permits the inner member to extend at least partially through the outer member 110. In a circumferential direction, opposite elongate slits 121 extend from the front end 120a of the inner member over a length, so that two arms 122 are formed. The width of the slits 121 is at least as large as the diameter of a rod to be inserted into the receiving part. Adjacent to the slits 121, two extensions 123 are formed that start at a distance above the free end 120a and extend beyond the free end 120a in the axial direction. The extensions 123 may have a cylindrical inner surface that matches the cylindrical outer surface of the receiving part 5. In addition, the extensions 123 may have a cylindrical outer surface corresponding to the outer surface of the outer member 110. The radial positions of the extensions 123 are such that, when the inner member 120 is in the outer member 110 and the slits 121 of the inner member and 111 of the outer member overlap, the extensions fill in the cutouts 113.

At the center of each of the arms 122 in the circumferential direction, two axially spaced apart protrusions 124, 125 are formed that are configured to engage the elongate recesses 115 on the arms 112 of the outer member 110. The first protrusion 124 may be substantially cuboid-shaped and is configured to be received in the upper portion 115a of the recess 115 of the outer member 110. The second protrusion 125 is spaced apart from the first protrusion 124 towards the front end 120a, and has a narrower neck portion 125a and a substantially plate-shaped head 125b. The neck portion 125a is configured to be guided between the wings 115c, and the head portion 125b is configured to extend over the wings 115c. When the inner member 120 is in the outer member 110 and the extensions 123 extend into the recesses 113, an axial movement of the inner member 120 relative to the outer member 110 is limited by the axial movement of the first protrusion 124 in the upper region 115a of the elongate recess 115. The extensions 123 can be moved beyond the front end 110a of the outer member 110 until the first protrusion 124 abuts against the wings 115c. It shall be noted that along the arms of the inner member and the outer member, further protrusions and recesses may be formed as depicted in FIG. 14. The displacement of the inner member relative to the outer member can be effected, for example, by using the rotating knob or handle 130.

The parts and portions of the bone anchoring device and the instrument may be made of any material, preferably however, of titanium or stainless steel or of any bio-compatible metal or metal alloy or plastic material. For bio-compatible alloys, a NiTi alloy, for example Nitinol, may be used. Other materials that can be use are, for example, magnesium or magnesium alloys. Bio-compatible plastic materials for use may be, for example, polyether ether ketone (PEEK) or poly-L-lactide ac-id (PLLA). The various parts can be made of the same or of different materials from one another.

Figure 22D:
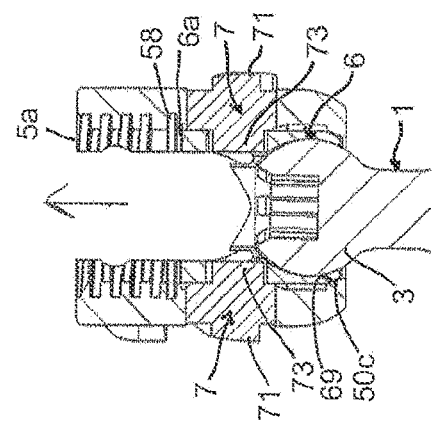
FIGS. 22a to 22d show cross-sectional views of the steps of mounting the coupling device to the bone anchor corresponding to FIGS. 21a to 21d, the cross-sections taken in a plane including a central axis of the coupling device and extending through middles of legs of the receiving part of the coupling device.
Figure 22C:
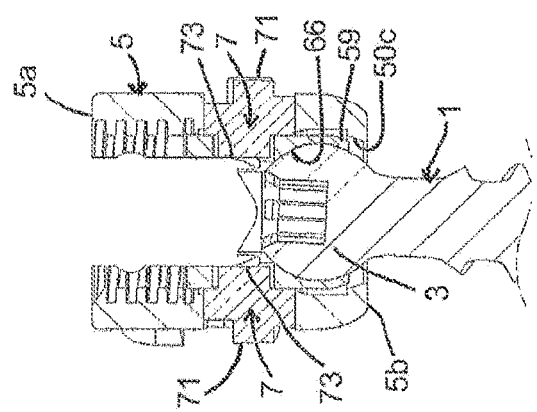

The actuating members 7 may preferably be preassembled with the receiving part. Once they have been inserted into the holes, a portion 57a of the outer edge of the holes 55 may be slightly deformed to provide an obstacle for the inserted actuating member in the outward direction (FIG. 22a). With the portion 57a, the actuating member may be prevented from being inadvertently pushed out of the hole 55 to the outside. The deformed portion 57a may be preferably at the bottom of the hole 55 in the direction towards the second end 5b of the receiving part 5. The orientation of the actuating members 7 in the holes is such that the lever-like protrusions 71 are on the outside and the cylindrical protrusions 73 extend into the recesses 600 of the pressure member 6, respectively. As the two actuating members 7 are identical, the free ends 71b of the lever-like protrusions 71 show in opposite directions when seen along the rod channel. Correspondingly, the cylindrical protrusions 73 are located at opposite ends 600a of the associated recesses 600 of the pressure member 6, respectively. When the actuating members 7 are actuated, they rotate in opposite directions.

The pressure member 6 may also be pre-assembled with the receiving part 5. For mounting, the pressure member 6 may be inserted through the first end 5a into the passage 50 of the receiving part 5 until the head receiving recess 66 extends into the accommodation space 50b. As the legs 63 of the pressure member 6 are slightly flexible, the outwardly extending rim 64 can slide along the inner wall of the threaded region in the receiving part until it snaps into the groove 58 when the pressure member 6 has reached a position in which the recesses 600 overlap with the holes 55, respectively. The rod support surface 62 is aligned with the substantially U-shaped recess 53 of the receiving part 5.

The coupling device preassembled in this way can be mounted to the bone anchor 1, either outside a patient's body or in-situ after the bone anchor 1 has been inserted into bone or a vertebra.

Figure 21D:
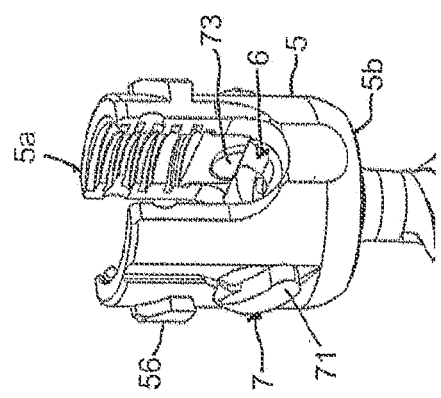
FIGS. 21a to 21d show perspective views of steps of mounting the coupling device of FIGS. 1 and 2 to a bone anchor of FIGS. 1 and 2 and pre-locking a head of the bone anchor in the coupling device.
Figure 21C:
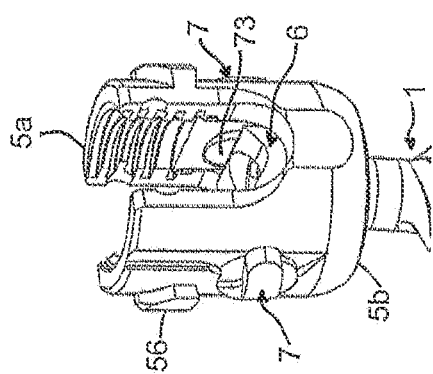

Assembly of the coupling device and the bone anchor will be described, referring to FIGS. 21a to 21d and the corresponding cross-sectional illustrations FIGS. 22a to 22d. First, as depicted in FIGS. 21a and 22a, the pressure member is in an insertion position, where the head receiving recess 66 is at least partially within the widened portion 50b of the passage 50 of the receiving part 5. The coupling device is oriented with the second end 5b of the receiving part towards the head 3 of the bone anchor. The cylindrical protrusions 73 of the actuating members 7 extend into the recesses 600, in which they can move to some extent. Moreover, the protrusions substantially prevent rotation of the pressure member 6 within the receiving part 5.

Figure 21B:
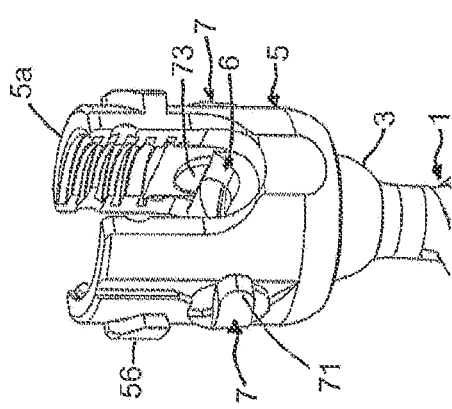
Figure 21A:
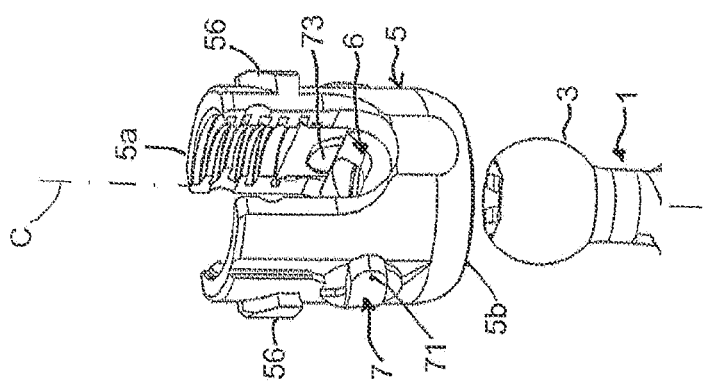
Figure 22B:
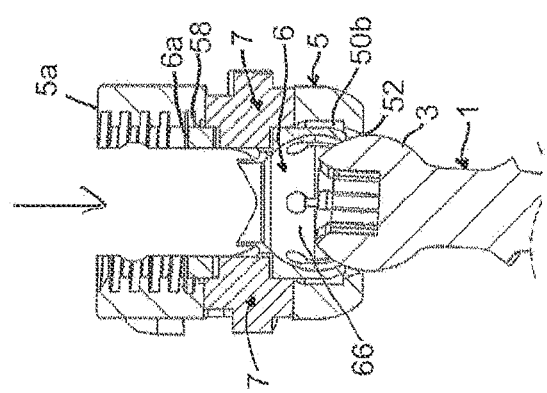
Figure 22A:
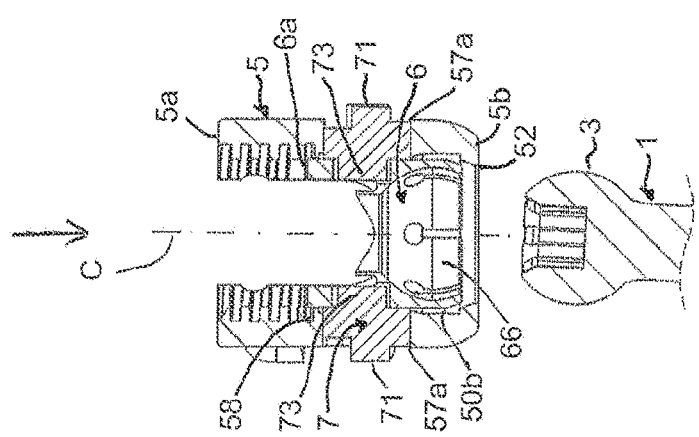

Next, as depicted in FIGS. 21b and 22b, the head 3 is inserted through the opening 52 at the second end 5b into the receiving part 5, and more particularly into the head receiving recess 66 of the pressure member 6. As the outwardly extending rim 64 abuts against an upper surface of the groove 58 in the receiving part, the pressure member 6 cannot be pushed out through the first end 5a of the receiving part 5 in this insertion position.

Further, as depicted in FIGS. 21c and 22c, the head 3 has fully entered the head receiving recess 66 of the pressure member. Due to the flexibility of the pressure member 6 in the region of the head receiving recess 66, the pressure member snaps onto the head 3. The widened portion 50b of the passage provides space for expansion of the pressure member therein when the head 3 is inserted. Depending on the size of the head receiving recess 66 relative to the head, the head 3 may be held by friction in the head receiving recess.

Finally, as shown in FIGS. 21*d* and 22*d*, the pressure member 6 is moved downward towards the second end 5*b* of the receiving part 5. Alternatively, when the bone anchor 1 has been inserted already into bone, the receiving part is pulled upwards relative to the bone anchor 1. By means of this, the outer surface portion 69 of the pressure member 6 enters the narrowing portion 50*c* of the passage 50, whereby the head 3 is prevented from being removed through the opening 52. This constitutes a pre-locking configuration. Preferably, in the pre-locking configuration, the head 3 is additionally clamped by friction and temporarily held at an angular position prior to final locking. The downward movement of the pressure member 6 into the pre-locking configuration causes the cylindrical protrusions 73 to move slightly within the recesses 600, respectively, which rotates the actuating members 7. As a result thereof, the lever-like protrusions 71 assume an inclined position.

Figure 23C:
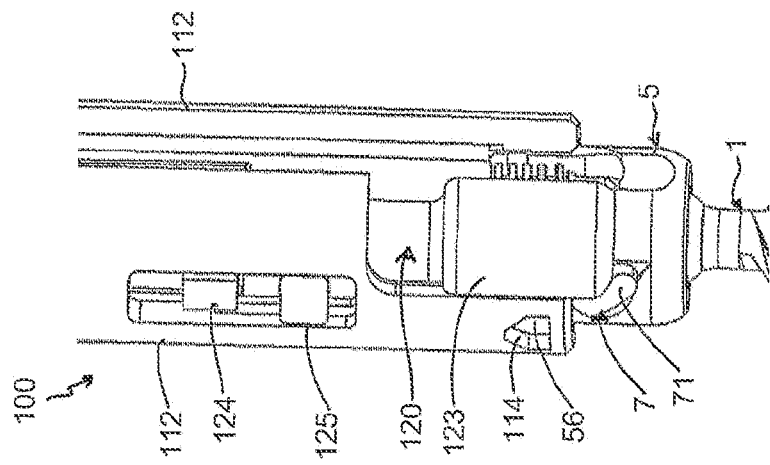
FIGS. 23a to 23c show perspective views of steps of attaching the instrument of FIG. 14 to the polyaxial bone anchoring device of FIGS. 1 and 2 and actuating the actuating portion with the instrument.
Figure 23B:
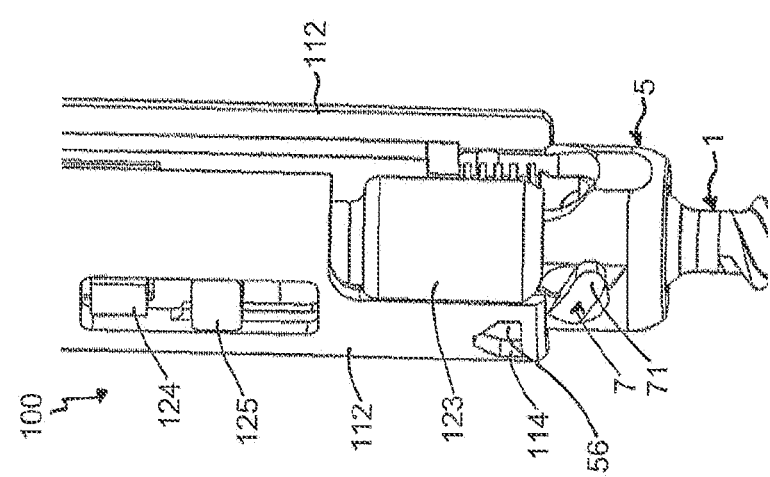
Figure 23A:
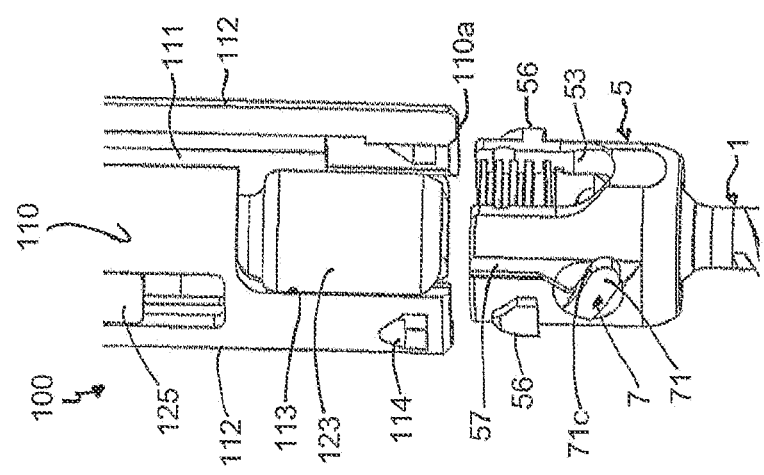

In clinical use, usually two or more bone anchors may be anchored in bone or in vertebrae and connected through a rod. FIGS. 23*a* to 23*c* show use of the bone anchoring device with the instrument described in FIGS. 14 to 20. The bone anchoring device is in the assembled and preferably in the pre-locked state as depicted in FIGS. 21*d* and 22*d*. In a first configuration of the instrument, the inner member 120 is in a retracted position, which means that the extensions 123 are substantially completely within the recesses 113. Preferably, in the first configuration, the front end 110*a* and the free ends of the extensions 123 are substantially flush with each other. The recesses 111, 121 of the instrument 100 are substantially aligned with the U-shaped recess 53 of receiving part 5. As shown in FIG. 23*a*, the instrument is moved towards the bone anchoring device.

Next, as shown in FIG. 23*b*, the instrument 100 is placed onto the receiving part and the outer member 110 is attached to the receiving part by engaging the engagement recesses 114 at the outer member 110 with the protrusions 56 of the receiving part. The beveled portion 56*c* at the roof of the protrusion 56 facilitates the engagement.

Finally, as shown in FIG. 23*c*, the inner member 120 is pushed downward so that the extensions 123 move in the axial direction out of the recesses 113 and press with their free ends on the engagement surface 71*c* of the lever-like protrusion 71 of the actuating members 7. When the lever-like protrusions 71 are pushed downward, the actuating members 7 are rotated to a small extent in the holes 55, respectively, which results in the pressure member 6 being moved further axially into the narrowing portion 50*c*, which locks the head 3.

Figure 24:
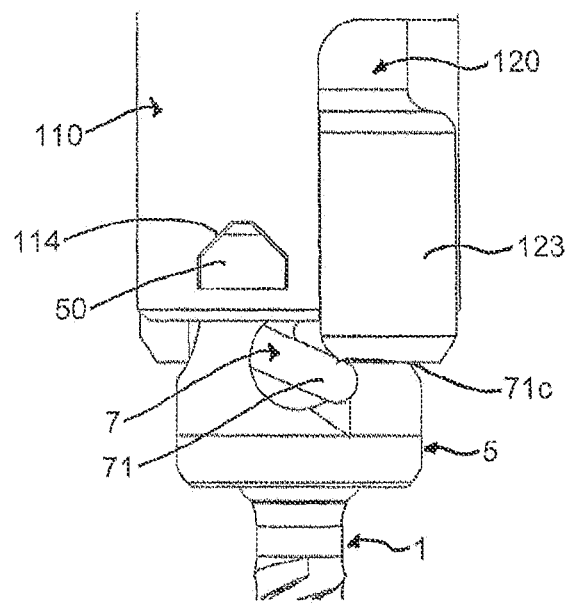
FIG. 24 shows a side view of a portion of the polyaxial bone anchoring device of FIGS. 1 and 2 with the instrument of FIG. 14 attached thereto and with the actuating portion in a first position.
Figure 25:
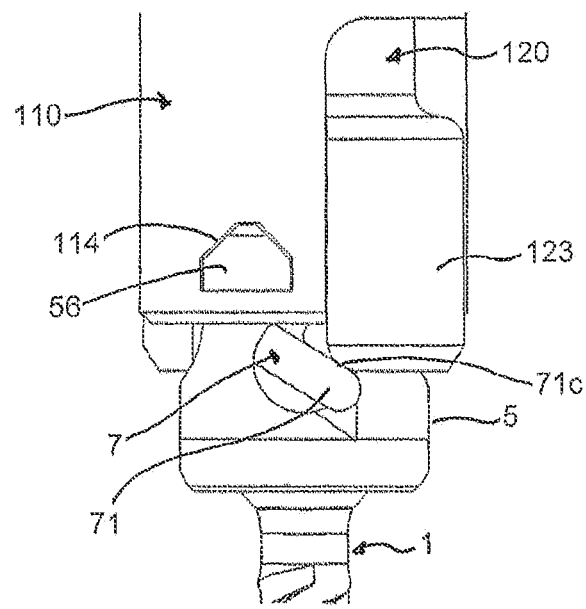
FIG. 25 shows a perspective view of a portion of the polyaxial bone anchoring device of FIGS. 1 and 2 with the instrument of FIG. 14 attached thereto and with the actuating portion in a second position.

FIGS. 24 and 25 show two configurations of the instrument and the bone anchoring device. In FIG. 24, the bone anchoring device is in the pre-locking configuration of FIGS. 21*d* and 22*d* and the lever-like protrusion 71 is only touched by the free end surface of the extension 123. In FIG. 25 the extension 123 has been pushed further downward to rotate the actuating member 7 by pressing onto the lever-like protrusion 71. In this configuration the head is temporarily locked by the instrument. As soon as the inner member 120 is retracted, the pressure is relieved and the head 3 is pivotable again within the head receiving recess 66 of the pressure member 6. It shall be noted that it may be possible by adjusting the force applied by the instrument to adjust the locking force on the head.

Figure 26:
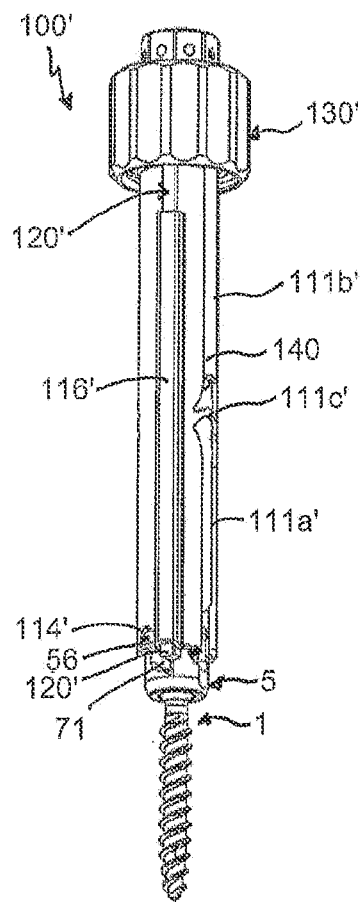
FIG. 26 shows a perspective view of another embodiment of a system including the polyaxial bone anchoring device of FIGS. 1 and 2 and another embodiment of an instrument attached thereto.
Figure 27:
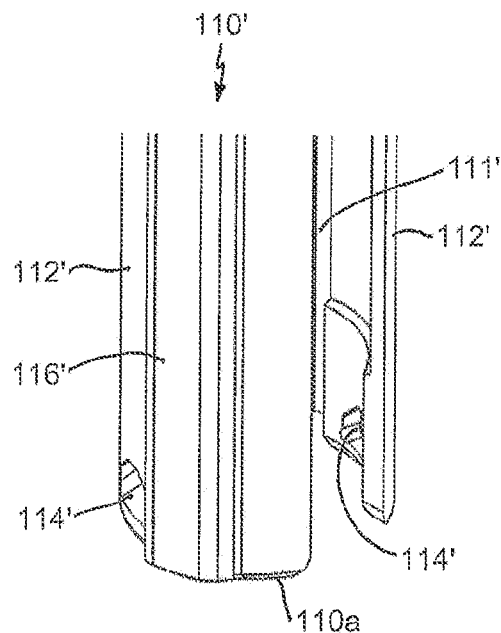
FIG. 27 shows a perspective view from a top of a front portion of an outer member of the instrument of FIG. 26.
Figure 28:
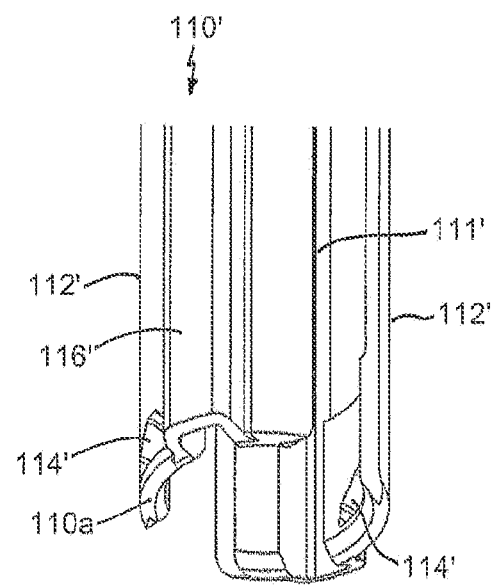
FIG. 28 shows a perspective view from a bottom of the front portion of FIG. 27.
Figure 29:
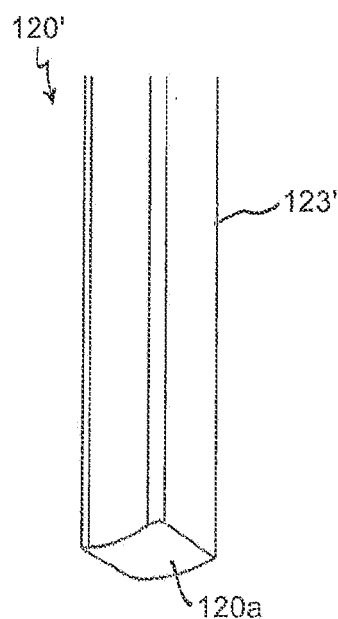
FIG. 29 shows a perspective view from a bottom of a front portion of an inner member of the instrument of FIG. 26.

A second embodiment of the instrument together with the polyaxial bone anchoring device of the first embodiment is shown in FIGS. 26 to 31. The descriptions of parts and portions of the instrument that are identical or similar to those of the first embodiment shall not be repeated, and such parts or portions have the same reference numerals as in the first embodiment. The instrument 100' has an inner member 120' that includes two bar-shaped pushing members 123' configured to press onto the lever-like protrusion 71 of the actuating member 7. As can be seen in FIG. 26, the outer member 110' has at each arm 112' an axially extending compartment 116' for guiding through the bar-shaped pushing member 123'. As additionally shown in FIGS. 27 and 28, the outer member 110' is a substantially tubular part with a front end 110*a* and which has two slits 111*a'*, 111*b'* separated by a bridging portion 111*c'*. The slits divide the outer member into two arms 112' which are free at the front end 110*a*. Each arm has at a distance from the front end 110*a* a recess 114' for engagement with the protrusion 56 of the receiving part. More specifically, the recesses 114' are arranged asymmetrical at positions corresponding to positions of the protrusions 56 at the receiving part, when the outer member is attached to the receiving part and the slits 111*a'*, 111*b'* and the substantially U-shaped recess 53 are aligned.

Each arm has an elongate compartment 116' for the pushing member 123'. The elongate compartment 116' extends from a distance from the rear end (not shown) of the outer member 110' up to the front end 110*a*, and is open towards the inside of the outer member 110'. An inner contour of the compartment 116' may substantially match an outer contour of the pushing member 123', so that the pushing member 123' is guided in the compartment 116'. The compartment 116' is at a position in the circumferential direction such that when the pushing member 123' extends through the compartment 116', the pushing member is configured to touch a forward region of the engagement surface 71*c* of the lever-like protrusion 71. Hence, the compartment 116' is offset from a center of the arm 112' in a circumferential direction and the two compartments 116' are arranged asymmetrically with respect to each other in the same manner as the lever-like protrusions 71 of the actuating members 7.

The pushing members 123' may have a square-shaped cross-section with rounded or flattened corners. The front end 120*a* may be convexly rounded. The pushing members 123' are connected to the outer member 110' in a manner such that rotating a handle or actuating member 130' displaces the pushing members 123' relative to the outer member 110'. It shall be noted that in the rearward portion of the outer member, a stabilization sleeve 140 may be provided that gives stability to the outer member 110'.

Figure 30:
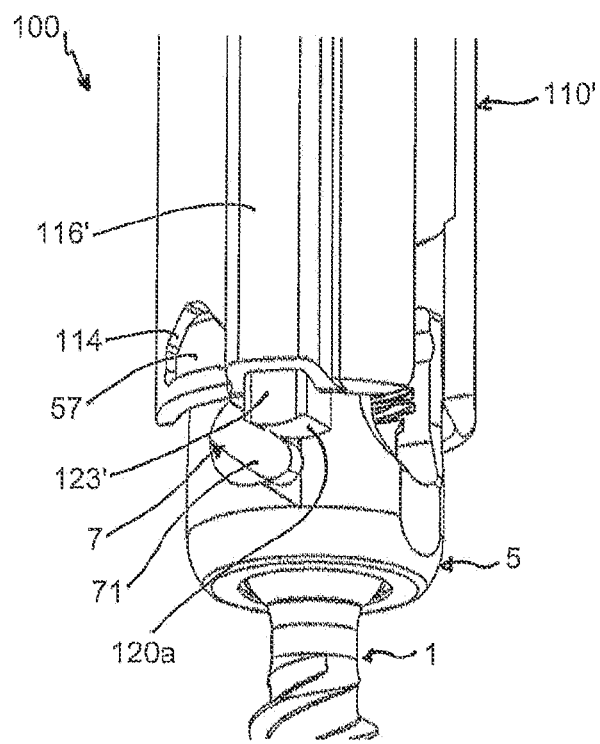
FIG. 30 shows a perspective view of a portion of the polyaxial bone anchoring device of FIGS. 1 and 2 with the instrument of FIG. 26 attached thereto.
Figure 31:
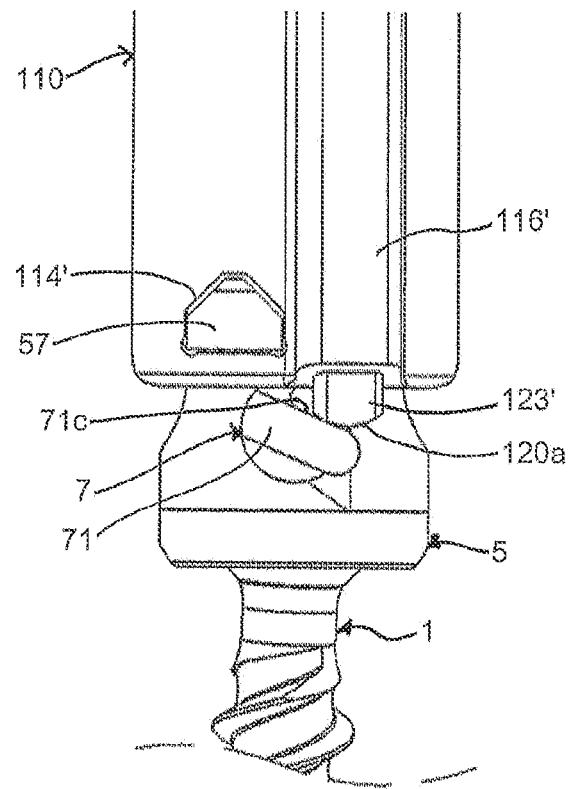
FIG. 31 shows a side view of the polyaxial bone anchoring device with the instrument of FIG. 30 attached thereto.

In use, as shown in FIGS. 30 and 31, the polyaxial bone anchoring device can be in the pre-locking condition as shown in FIGS. 21*d* and 22*d*, when the instrument 100' is attached to the receiving part 5. The arms 112' are slightly spread apart so that the recesses 114' of the outer member 110' can engage the protrusions 56 of the receiving part 5. The pushing members 123' are moved out of the compartment 116' until they press with their front surface 120*a* onto the engagement surface 71*c* of the lever-like protrusion 71. Since the front surface 120*a* of the pushing member is rounded, a sufficient contact between the end surface 120*a* and the engagement surface 71*a* can be achieved. Each pushing member 123' presses the lever-like protrusion 71 downward, whereby the corresponding actuating member 7 rotates within the hole. As in the first embodiment, the cylindrical protrusion 73 moves downward and pushes the pressure member 6 deeper into the narrowing portion 50c of the receiving part. As a result thereof, the head 3 is temporarily locked as long as the pushing member 123' presses onto the lever-like protrusion 71. When the pushing members are retracted, the pressure exerted onto the pressure member by the actuating member 7 is relieved and the head is pivotable again.

A third embodiment of the instrument and a modified embodiment of the receiving part will be described, referring to FIGS. 32 to 47. Parts and portions of the polyaxial bone anchoring device that are identical or similar to the polyaxial bone anchoring device of the previous embodiments have the same reference numerals, and the descriptions thereof will not be repeated.

The polyaxial bone anchoring device includes the bone anchor 1 as in the previous embodiments and a modified receiving part 5', a modified pressure member 6', and modified actuating members 7'. Referring more in detail to FIGS. 33 to 38, the passage 50 in the receiving part 5' includes a substantially conically tapering section 50c' that extends from the second end 5b over a region of the head receiving recess of the pressure member that includes the greatest diameter of the head and that is configured to cooperate with a corresponding conically tapering outer surface of the pressure member 6' as described below. The conically tapering section 50c' is interrupted in the axial direction by a widened portion 50b' that has an enlarged inner diameter, for permitting the pressure member 6' to expand therein during insertion of the head 3. The holes 55' for receiving the actuating members 7 are, as in the first embodiment, located in the middle of each leg 54 in the circumferential direction and extend in the axial direction above the bottom 53a of the substantially U-shaped recess 53. Between an upper edge of each hole 55 in the direction of the first end 5a, an engagement protrusion 56' is provided that is symmetrical to the center of each leg 54 in the circumferential direction. The engagement protrusion 56' may have the same or a similar shape as in the previous embodiments, i.e., the protrusion has a base and a roof-shaped upper portion. The groove in the outer surface of the receiving part may be omitted.

The pressure member 6' has an upper portion 60 that is identical to the upper portion of the previous embodiments. The lower portion 61' includes a conically-shaped outer surface 69' that extends over an axial height that includes the portion with the greatest diameter of the head when the head is inserted. When the pressure member 6' is in the receiving part 5', the outer conical surface portion 69' contacts the conically tapered portion 50c' above and below the widened portion 50b'.

The actuating members 7' in this embodiment include the cylindrical main portion 70 and the cylindrical eccentric protrusion 73 protruding from the inside face 70b as in the first embodiment. On the outside face 70a, an engagement portion for the instrument is formed as a cylindrical protrusion 71', which may also be arranged eccentrically relative to the main portion 70 and arranged at the same position as the cylindrical protrusion 73 but on the opposite side of the main portion 70. The cylinder axis z' of the cylindrical protrusion 71' is offset from the axis of rotation R of the main portion 70. The size of the cylindrical protrusion 71' may be the same as that of the cylindrical protrusion 73. Moreover, the cylinder axes of the cylindrical protrusions 71', 73 may be coincident. On the outside face 70a, a cutaway portion 74 or other marking may be provided for orienting the actuating member properly in the hole 55. More specifically, referring in particular to FIG. 34, the actuating members 7' are mounted to the receiving part 5' in a manner such that the cylinder axis z' is offset from the center of the leg 54 in the circumferential direction. In this way, the protrusion 71' functions similar to the lever 71 of the previous embodiments.

As depicted in FIG. 45a, the instrument 100" includes an outer member 110" that is substantially tube-shaped and an inner member 120", also substantially tube-shaped and guided in the outer member 110". The outer member 110" has, at its front end 110a, a substantially rectangular recess 111" that divides the front portion into two arms 112". A width of the recess 111" is such that the arms 112" are spaced apart from each other so as to permit the front portion to be placed over the receiving part 5'. The axial length of the recess 111" is such that when the front portion has been placed onto the receiving part, there is still space in the axial direction that permits insertion of the rod. The inner wall of the arms 112" each has, at a distance from the front end 110a, a recessed portion 113' that serves for receiving a front portion of the inner member 120" therein. On an inner wall of the arms 112" at a distance from the front end 110a, an engagement recess 118" is formed that has the contour of substantially an U rotated by 90°, so that the recess is open in the circumferential direction to one edge of the arm 112". The engagement recess 118" at the opposite arm 112" is open in the same direction (i.e., towards the opposite side of the recess 111"). The contour of the recess 118" is such that the cylindrical protrusion 71' of the actuating member 7' can be received and guided therein. When the instrument is placed on the receiving part 5' at a lateral or circumferentially offset position relative to the engagement protrusions 71' of the actuating members 7', rotation of the instrument towards the protrusions 71' causes the engagement recesses 118" to engage the corresponding engagement protrusions 71'.

Figure 32:
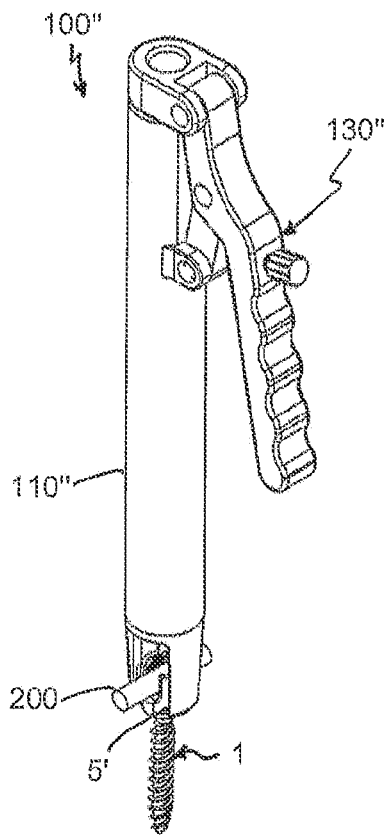
FIG. 32 shows a perspective view of a further embodiment of a system including a further embodiment of a polyaxial bone anchoring device and a further embodiment of an instrument.
Figure 33:
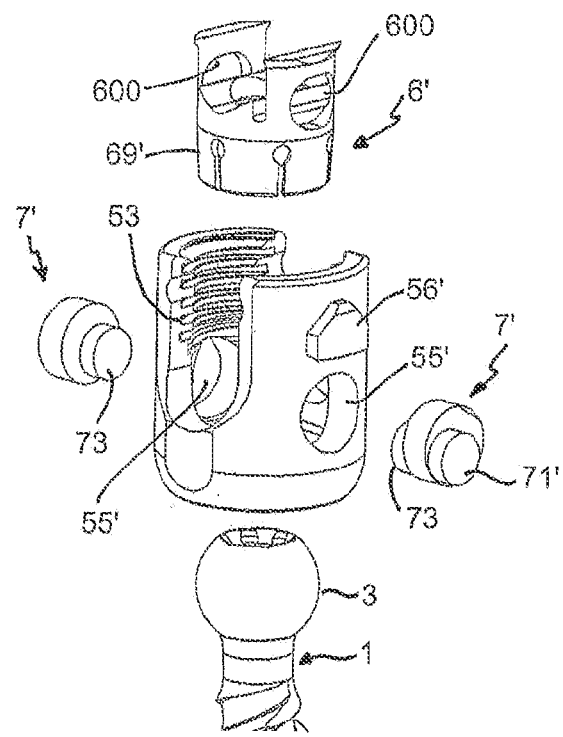
FIG. 33 shows a perspective exploded view of the embodiment of the polyaxial bone anchoring device of FIG. 32.
Figure 34:
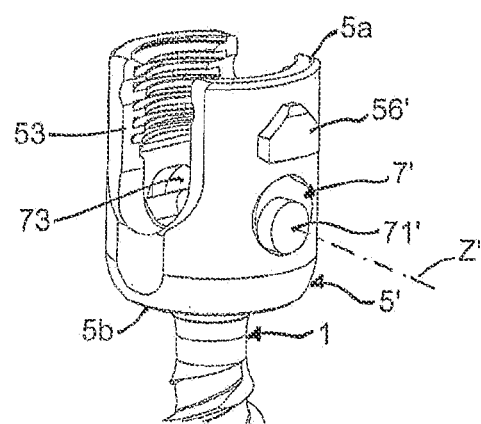
FIG. 34 shows a perspective view of the polyaxial bone anchoring device of FIG. 33 in an assembled state.
Figure 35:
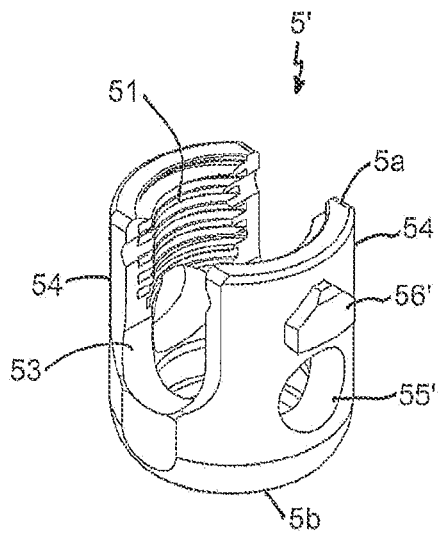
FIG. 35 shows a perspective view from a top of a receiving part of the polyaxial bone anchoring device of FIGS. 32 to 34.
Figure 36:
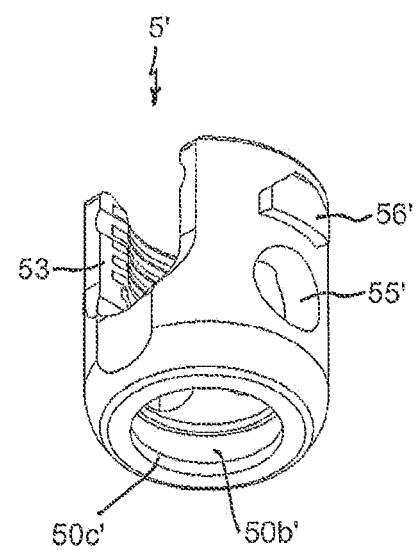
FIG. 36 shows a perspective view from a bottom of the receiving part of FIG. 35.
Figure 37:
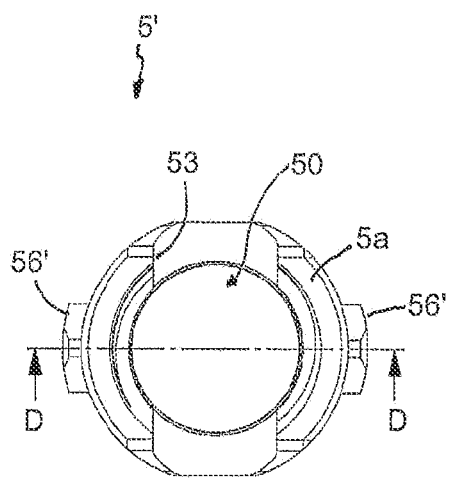
FIG. 37 shows a top view of the receiving part of FIGS. 35 and 36.
Figure 38:
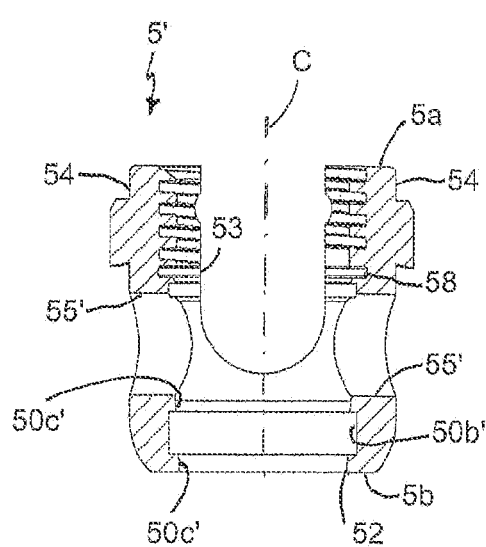
FIG. 38 shows a cross-sectional view of the receiving part of FIGS. 35 to 37, the cross-section taken along line D-D in FIG. 37.
Figure 39:
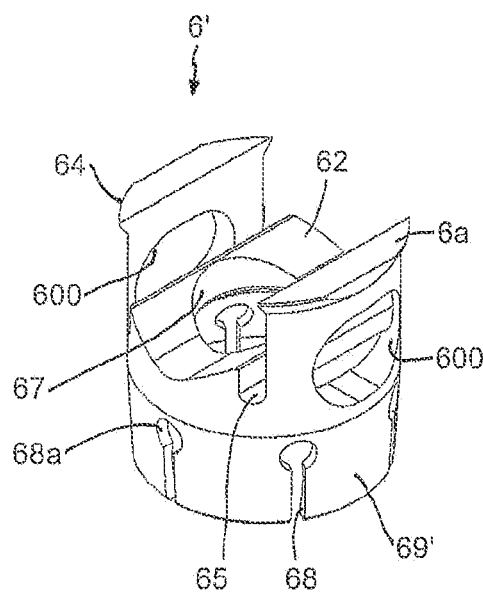
FIG. 39 shows a perspective view from a top of the pressure member of the polyaxial bone anchoring device of FIGS. 32 to 34.
Figure 40:
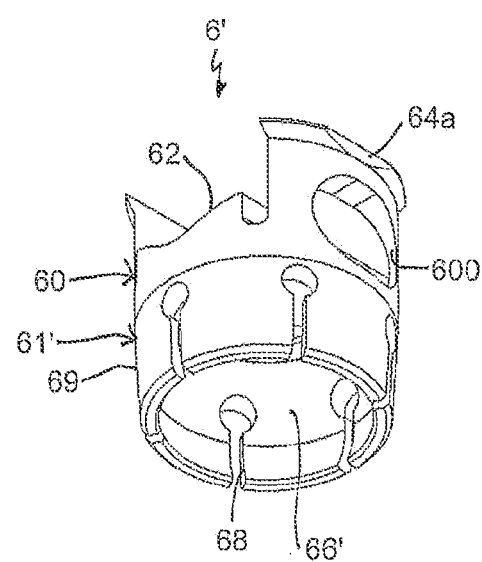
FIG. 40 shows a perspective view from a bottom of the pressure member of FIG. 39.
Figure 41:
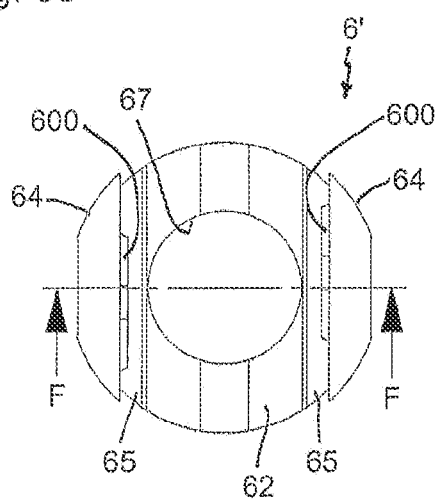
FIG. 41 shows a top view of the pressure member of FIGS. 39 and 40.
Figure 42:
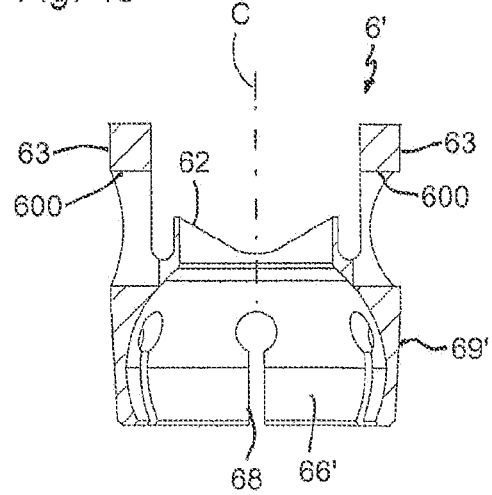
FIG. 42 shows a cross-sectional view of the pressure member of FIGS. 39 to 41, the cross-section taken along line F-F in FIG. 41.

The inner member 120" is displaceable with respect to the outer member 110" by a mechanism 130" that may include a lever 130", for example (FIG. 32). Various other mechanisms may be used to displace the inner member relative to the outer member. The front portion of the inner member 120" includes, at the front end 120a, two arms 122". The arms 122" may be guided within the arms 112" of the outer member 110". At the inner wall of each of the arms 122", an engagement recess 126" is formed that has on one side a shape matching the shape of the protrusion 56' of the receiving part and that is open in the circumferential direction on the other side. The engagement recesses 126" on the inner member are positioned and shaped so as to permit engagement with the engagement protrusions 56' of the receiving part 5' when the instrument is placed onto the receiving part and rotated in one direction.

In use, as depicted in FIGS. 45a and 45b, the arms of the instrument are placed over the receiving part 5' laterally or circumferentially offset from the engagement protrusions 56'. A rod 200 may be inserted already into the recess 53.

Next, as shown in FIG. 45c, the instrument is rotated until the engagement recesses 126" of the inner member 120" engage the engagement protrusions 56' of the receiving part 5', and simultaneously the engagement recesses 118" of the outer member 110" engage the engagement protrusions 71' of the actuating members 7'.

Thereafter, as shown in FIG. 45d, the outer member 110" is displaced relative to the inner member 120" downward in a direction towards the second end 5b of the receiving part 5'. The outer member exerts a force onto the engagement protrusions 71', so that the actuating members 7' rotate around the axis of rotation R. Simultaneously, the eccentric protrusions 73 move downward and, as a result, the pressure member 6' is pressed farther into the conical section 50c" of the passage to lock the head 3.

In this embodiment, the outer member 110" can be retracted with respect to the inner member 120". The bottom edge of the recess 118" moves the protrusion 71' upward and the pressure member follows the upward movement so that the temporary locking of the head 3 can be released.

The locking and releasing of the head 3 can be performed several times until a correct position of the bone anchor 1 relative to the receiving part 5' can be found. Generally, the rod 200 may already be inserted into the recess 53 of the receiving part, as shown in the figures, the recess 53 may remain unobstructed, and/or the rod 200 may be inserted during the correction steps. The instrument can be released by rotating the instrument in the opposite direction to effect the disengagement of the protrusion 56' from the recess 126' and the protrusion 71' from the recess 118'.

Figure 47:
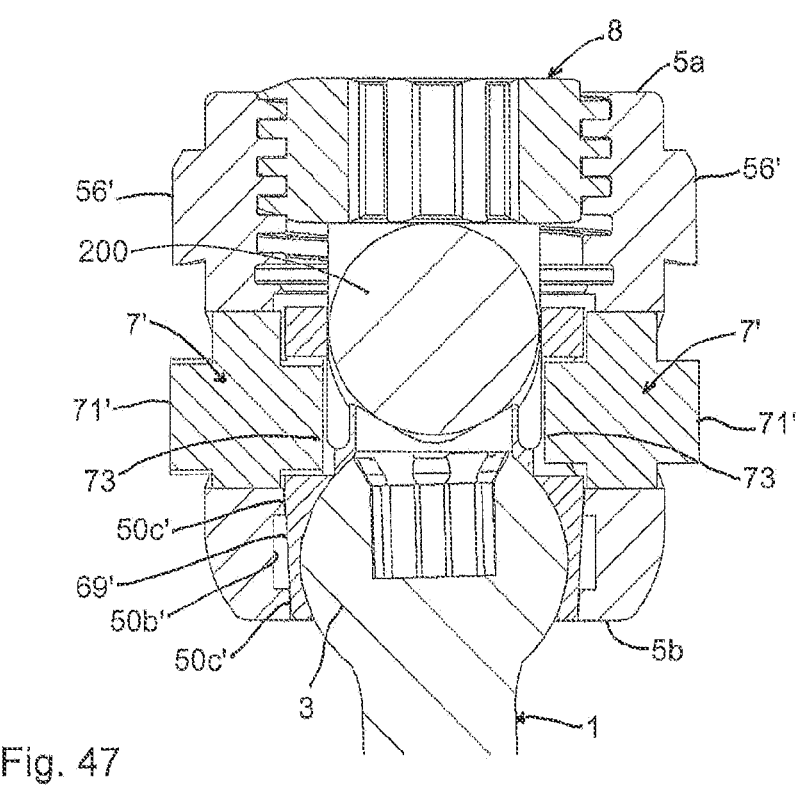
FIG. 47 shows a cross-sectional view of the polyaxial bone anchoring device of FIGS. 32 to 34, with the instrument removed and the rod fixed.
Figure 48:
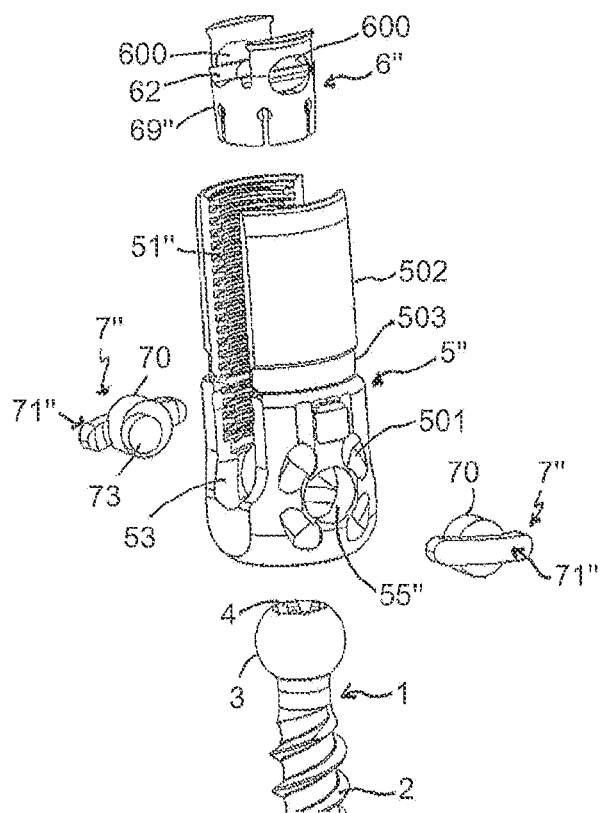
FIG. 48 shows a perspective exploded view of a still further embodiment of the polyaxial bone anchoring device.
Figure 49:
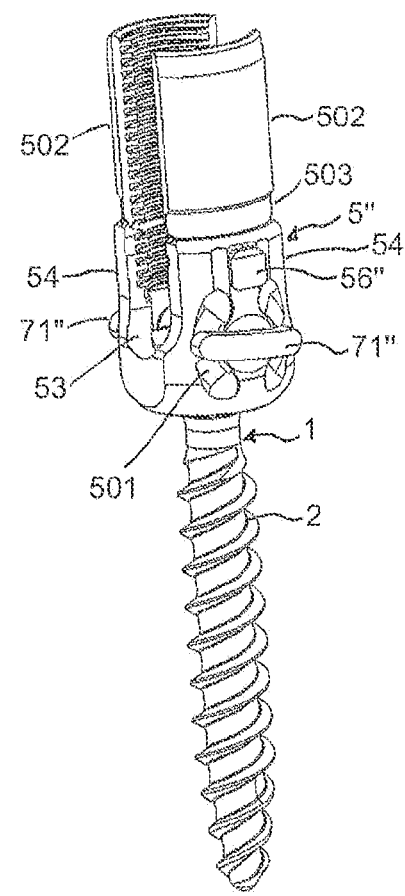
FIG. 49 shows a perspective view of the polyaxial bone anchoring device of FIG. 48 in an assembled state.
Figure 50:
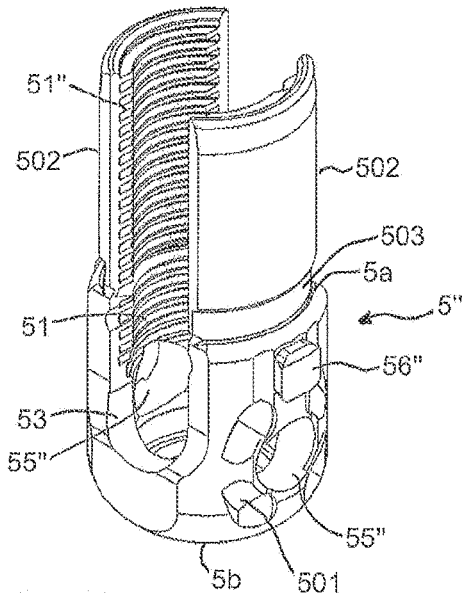
FIG. 50 shows a perspective view from a top of a receiving part of the polyaxial bone anchoring device of FIGS. 48 and 49.
Figure 51:
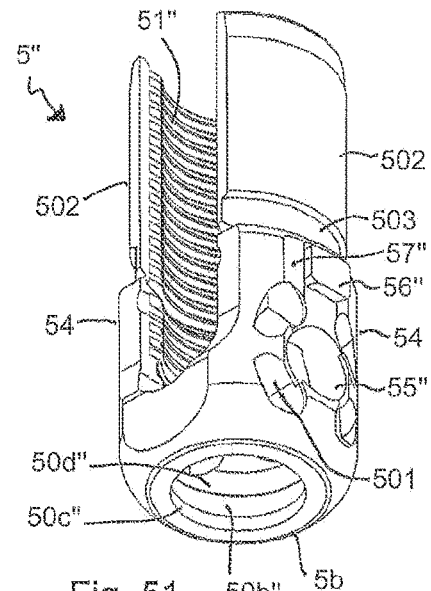
FIG. 51 shows a perspective view from a bottom of the receiving part of FIG. 50.
Figure 52:
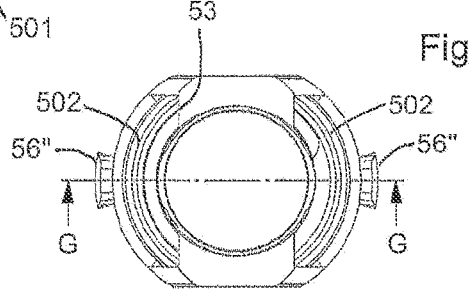
FIG. 52 shows a top view of the receiving part of FIGS. 50 and 51.
Figure 53:
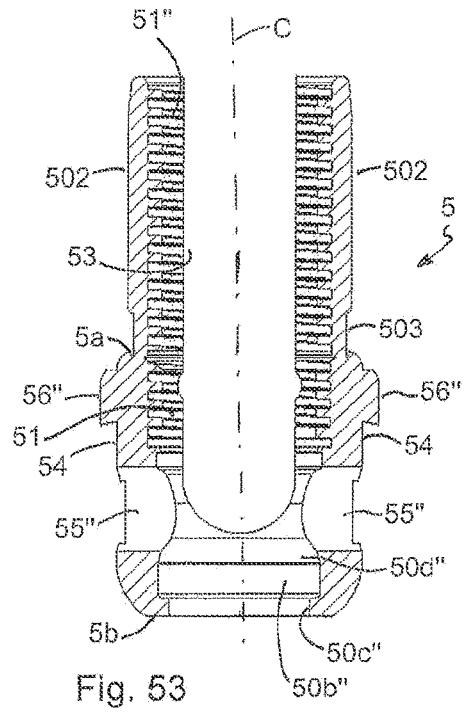
FIG. 53 shows a cross-sectional view of the receiving part of FIGS. 50 to 52, the cross-section taken along line G-G in FIG. 52.
Figure 54:
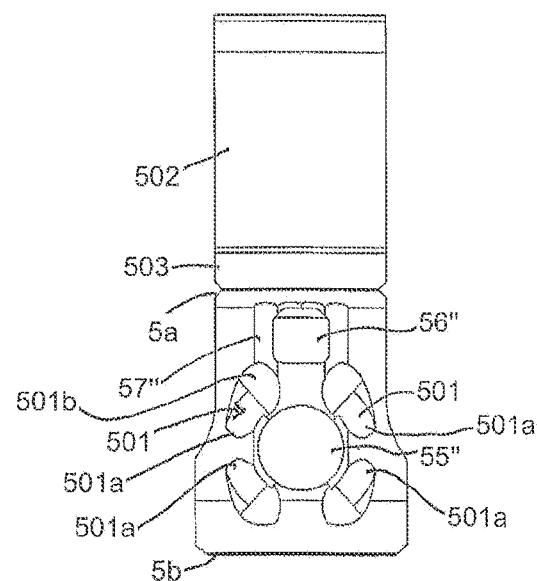
FIG. 54 shows a side view of the receiving part of FIGS. 50 to 53.
Figure 55:
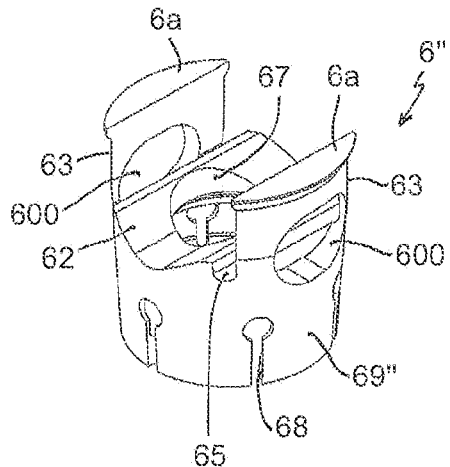
FIG. 55 shows a perspective view from a top of a pressure member of the polyaxial bone anchoring device of FIGS. 48 and 49.
Figure 56:
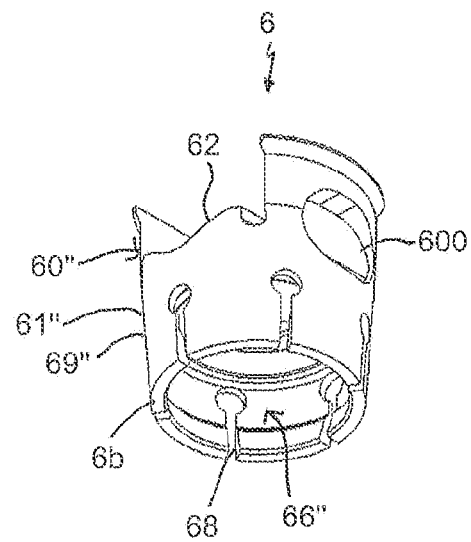
FIG. 56 shows a perspective view from a bottom of the pressure member of FIG. 55.
Figure 57:
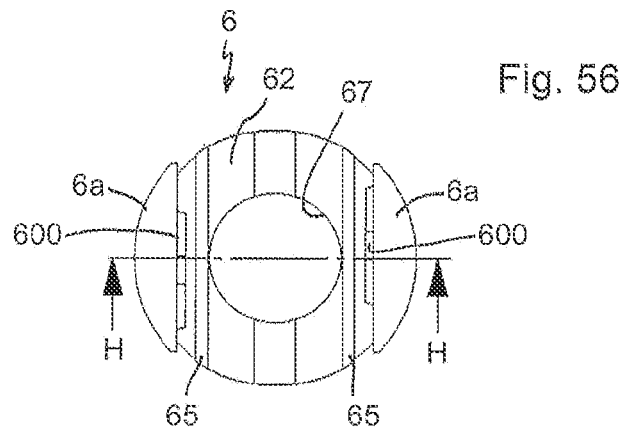
FIG. 57 shows a top view of the pressure member of FIGS. 55 and 56.
Figure 58:
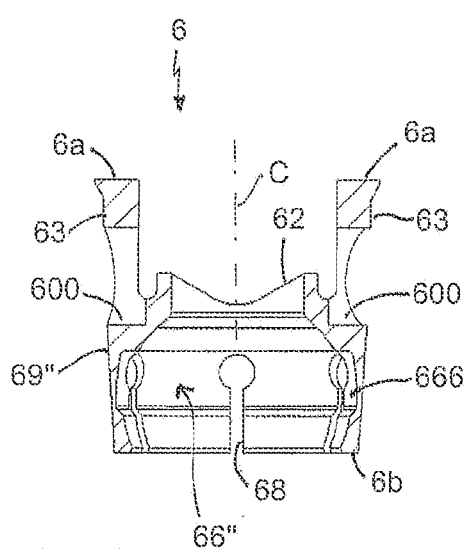
FIG. 58 shows a cross-sectional view of the pressure member of FIGS. 55 to 57, the cross-section taken along line H-H in FIG. 57.
Figure 59:
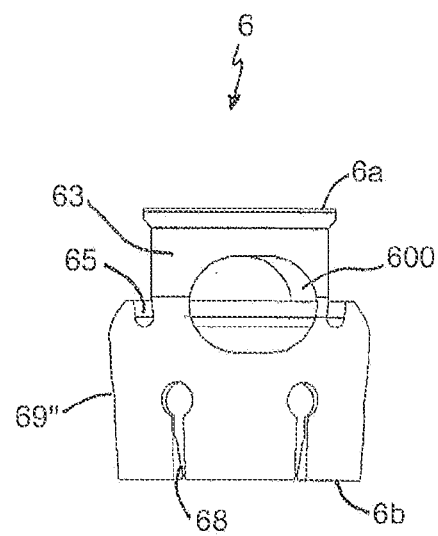
FIG. 59 shows a side view of the pressure member of FIGS. 55 to 58.
Figure 60:
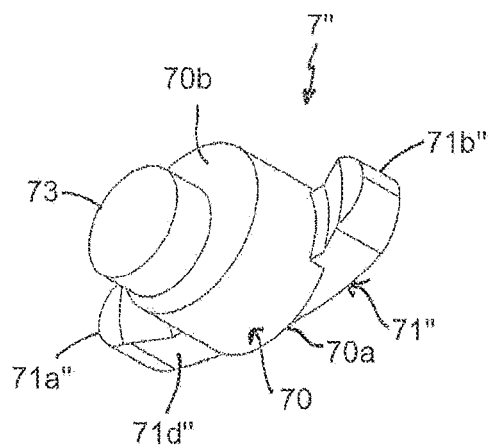
FIG. 60 shows a perspective view from a bottom of an actuating portion of the polyaxial bone anchoring device of FIGS. 48 and 49.
Figure 61:
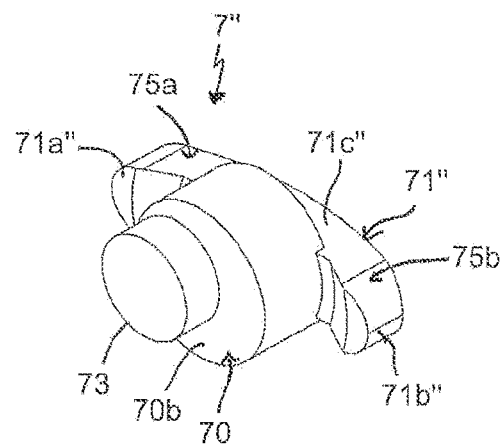
FIG. 61 shows a perspective view from a top of the actuating portion of FIG. 60.

As depicted in FIG. 47, once the correct angular position of the bone anchor 1 relative to the receiving part 5' has been found and the rod has been inserted, a fixation member 8, in this embodiment a set screw, can be inserted between the legs and tightened to fix the rod and the head. The rod or the fixation member can also be inserted before correction or locking of the polyaxial angle, for example, via the instrument, takes place.

A still further embodiment of the polyaxial bone anchoring device and an instrument for use with such a polyaxial bone anchoring device is shown in FIGS. 48 to 69b. Parts and portions that are identical or similar to the parts and portions of the previous embodiments are marked with the same reference numerals. Referring to FIGS. 48 to 54, the receiving part 5" is similar to the receiving part 5' of FIGS. 35 to 38, with some details being different. The accommodation space for accommodating a portion of the pressure member includes a conically tapering lower section 50c" close to the second end 5b that is configured to cooperate with a conical outer surface of the pressure member. Adjacent to the conical section 50c", a cylindrical widened portion 50b" permits the pressure member to expand during insertion of the head 3. Above the widened portion 50b", an upper portion 50d" provides space for an upper region of a conical portion of the pressure member. Around the holes 55" that are located in the center of the legs 54 in a circumferential direction, a plurality of, preferably shallow, recesses 501 are formed in the outer wall of the receiving part 5". The recesses 501 are shaped and sized to accommodate a portion of the actuating member 7" therein. In greater detail, the recesses 501 may be oblong and slightly drop shaped, with a narrow end 501a and an opposite broad end 501b. In the embodiment, four such recesses 501 are provided that are arranged close to the corners of a virtual square around the hole 55", such that the narrow ends 501a face each other, respectively.

The protrusions 56" for engagement with the instrument are located in the middle of the legs 54 in the circumferential direction, above the holes 55", respectively. In this embodiment, the protrusions 56" have a substantially rectangular-contoured base and a low roof-shaped portion in the direction of the first end 5a. The protrusion 56" may be framed by two axial grooves 57" for guiding the instrument.

Lastly, the receiving part 5" has two extensions 502 that extend from the legs 54 above the first end 5a, and which have a length such that they are configured to protrude out of a patient's skin when the polyaxial bone anchoring device is inserted into bone or a vertebra. The extensions 502 may have at least in a portion thereof an internal thread 51" that continues into the internal thread 51 on the legs 54. The purpose of the extensions 502 is to allow for easier guidance of the instruments and parts, such as for example a fixation screw, from outside to the receiving part 5". Adjacent to the first end 5a, which in this case is the outer end of the legs 54, a weakened section 503 is formed on each leg 54 that has a reduced thickness in the radial direction which permits breaking off of the extensions 502 from the receiving part 5". The extensions 502 can be removed once the polyaxial bone anchoring device has been inserted and once the extensions are no longer needed, preferably after locking of the head and fixation of the rod.

The pressure member 6" has an upper substantially cylindrical portion 60" and a lower conical portion 61". The pressure member 6" differs from the pressure member 6' of FIGS. 39 to 42 in that the lower portion 61" includes a conical outer surface portion 69" that extends in the axial direction up to about the middle of the recesses 600 for the actuating portions 7". As in the previous embodiments, the recesses 600 are located offset from the center of the legs 63 of the pressure member 6" to opposite sides. As can be seen in particular in FIG. 58, the head receiving recess 66" may have, at a distance from the second end 6b, an enlarged conical section 666 that widens towards the second end 6b. This may facilitate pivoting of an inserted head in the head receiving recess 66' to greater angles.

Figure 43:
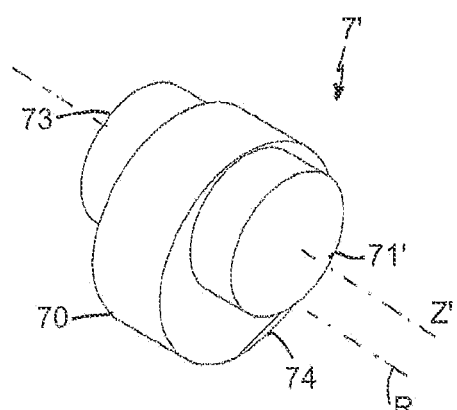
FIG. 43 shows a perspective view of an actuating portion of the polyaxial bone anchoring device of FIGS. 32 to 34.
Figure 44:
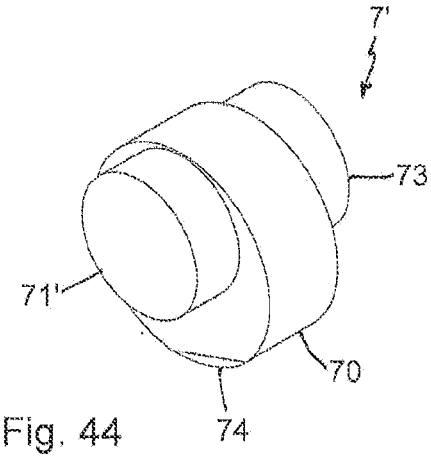
FIG. 44 shows another perspective view of the actuating portion of FIG. 43.
Figure 45:
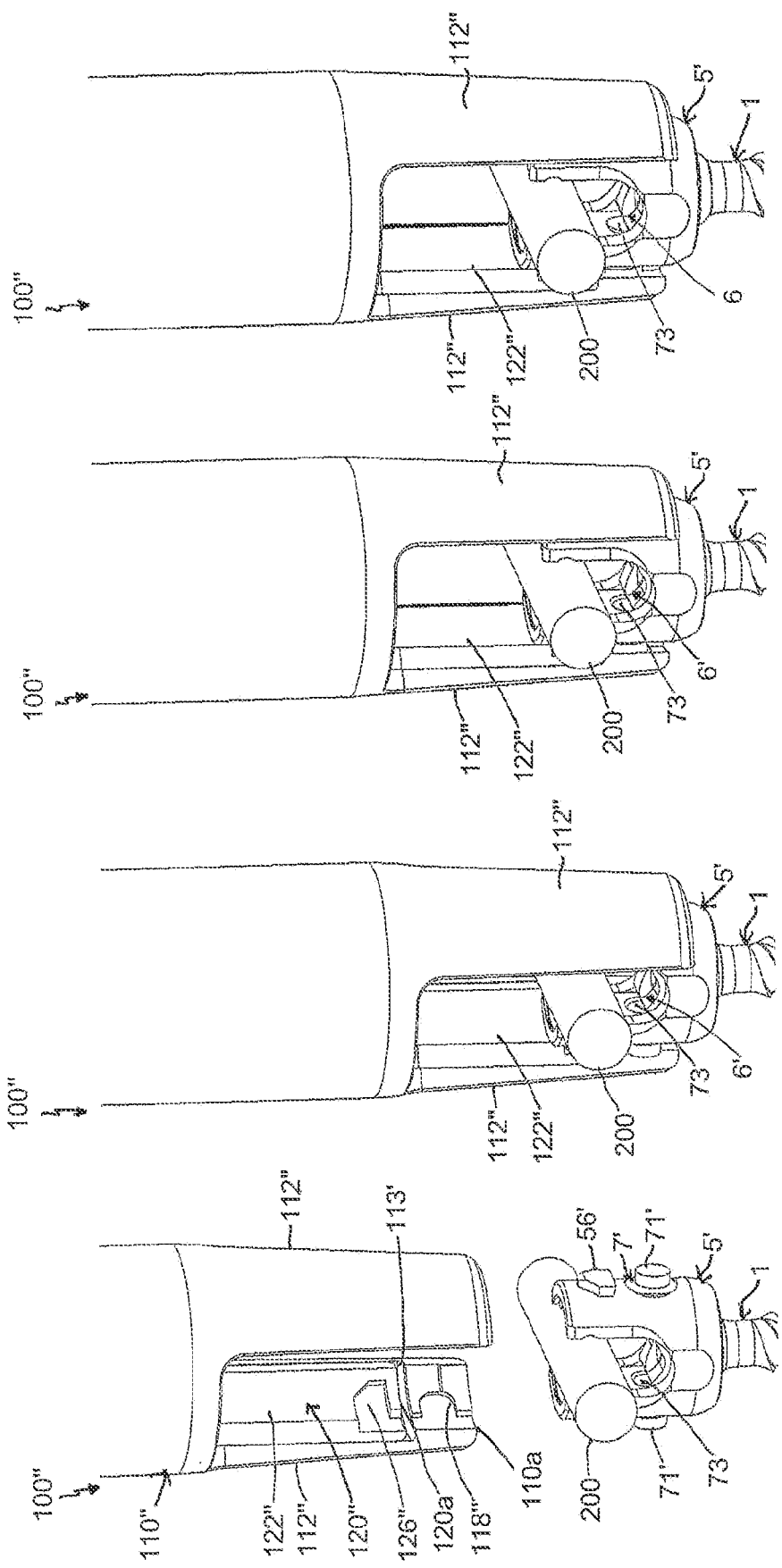
FIGS. 45a to 45d show perspective views of steps of attaching and actuating the instrument of FIG. 32 relative to the polyaxial bone anchoring device of FIGS. 32 to 34, with a rod placed in a recess for the rod that is formed on the receiving part.
Figure 46:
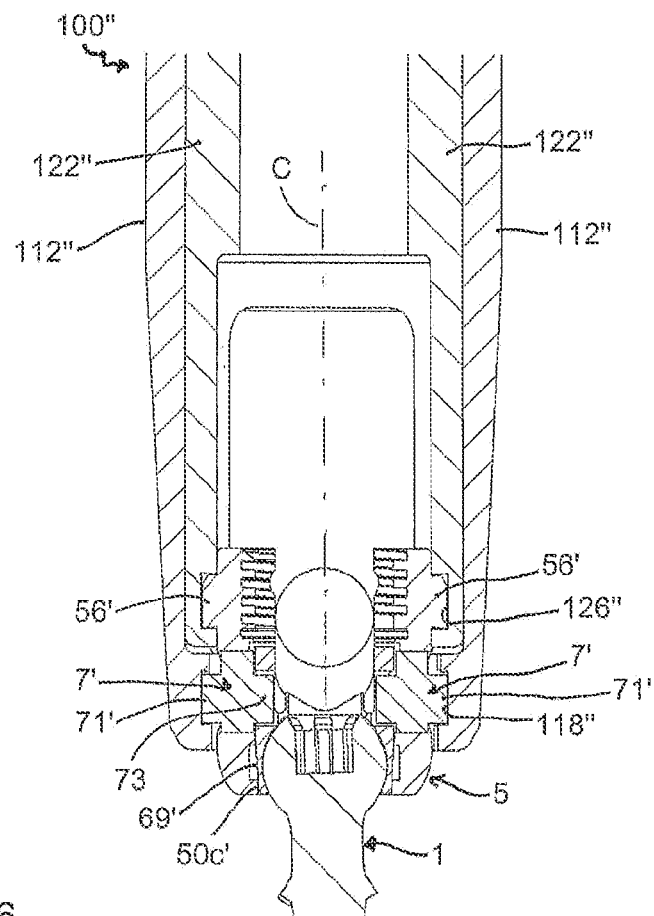
FIG. 46 shows a cross-sectional view of the polyaxial bone anchoring device of FIGS. 32 to 34 and the instrument of FIG. 32 attached thereto with an inserted rod, the cross-section taken in a plane including the central axis of the receiving part and extending through centers of legs of the receiving part.
Figure 62:
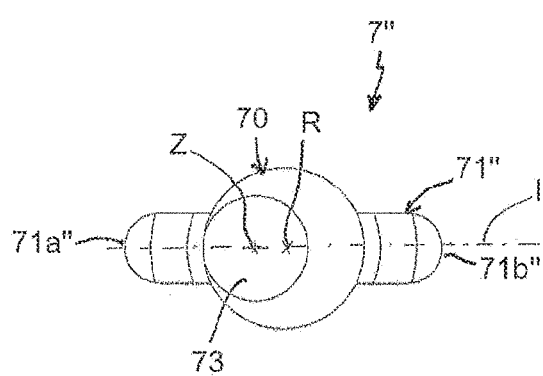
FIG. 62 shows a top view of the actuating portion of FIGS. 60 and 61.
Figure 63:
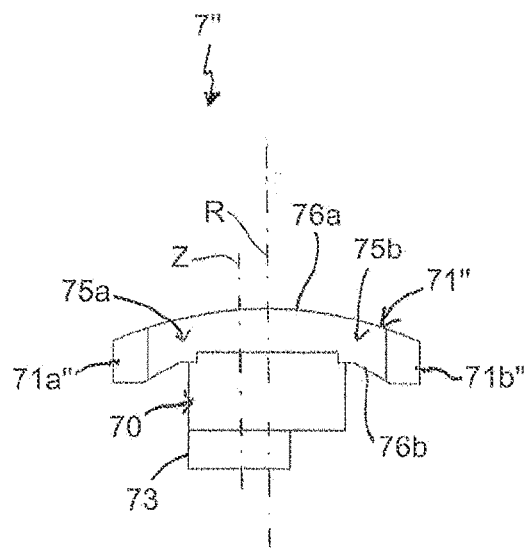
FIG. 63 shows a side view of the actuating portion of FIGS. 60 to 62.

Referring to FIGS. 60 to 63, the actuating portion 7" includes the cylindrical main portion 70 and the cylindrical eccentric protrusion 73 protruding from the inside face 70b of the main portion 70, similarly as in the embodiment according to FIGS. 43 to 44. The cylinder axis z of the cylindrical protrusion 73 is offset from the axis of rotation R of the main portion 70. On the outside face 70a of the main portion 70, a bar 71" is formed that is configured to be engaged by an instrument. The bar 71" preferably extends with both its free end portions 71a", 71b" beyond the outside contour of the main portion 70. The bar 71" functions like a two-armed lever with the pivot axis of the lever being coaxial with the axis of rotation R of the main portion 70. In greater detail, one lever arm 75a extends from the pivot axis to one free end 71a" and the other lever arm 75b extends from the pivot axis to the opposite free end 71b". The bar 71" is oriented with respect to the eccentric protrusion 73 such that the longitudinal axis I of the bar 71" is substantially parallel to a line that connects the axis of rotation R of the main portion 70 and the axis of rotation z of the eccentric portion 73 in a top view, as shown in FIG. 62. Hence, the bar 71" is substantially aligned with the eccentric protrusion 73. Moreover, the bar 71" may have a convex outer surface 76a that faces away from the cylindrical main portion 70 and a concave inner surface 76b that faces towards the main portion 70. The end portions 71a", 71b" may be somewhat thicker in the direction of the main portion 70 to provide more stability to the bar 71". When the actuating portions 7" are inserted in the respective holes 55" of the receiving part 5" and oriented such that the longitudinal axis I of the bar 71" extends substantially perpendicular to the central axis C of the receiving part 5", the end portions 71a", 71b" of the bar 71" touch the outer surface of the receiving part 5" between two recesses 501. When the lever is pivoted, the thickened end portions 71a", 71b" move into the recesses 501. This allows the design of the receiving part with the actuating portions to be more compact. The bar 71" has a first lever surface 71c" and an opposite second lever surface 71d" that are oriented substantially parallel to the axis of rotation R of the main portion 70 and that can be engaged by an instrument, depending on which one of the surfaces is oriented towards the instrument. The two actuating portions 7" are arranged in the holes 55" of the receiving part 5" such that for one of the actuating portions 7", the first lever surface 71c" faces towards the first end 5a of the receiving part 5", and for the other actuating portion 7", the second lever surface 71d" faces towards the first end 5a of the receiving part 5".

Referring to FIGS. 64 to 67, an instrument that is suitable for use with the bone anchoring device according to FIGS. 48 to 63 will be explained. The instrument includes a first instrument portion or outer member 1100 in the form of a substantially tubular part with a front end 1100a and two slits 1111 each bridged by a bridging portion 1112. The slits 1111 divide the first instrument portion 1100 into two arms 1120, which may be slightly flexible such that they can be clipped on the receiving part 5". Each arm 1120 has, at a distance from the front end 1100a, a recess 1140 for engagement with the protrusions 56" of the receiving part 5". More specifically, the recesses 1140 are arranged in the middle of each of the arms 1120 in the circumferential direction at positions corresponding to positions of the protrusions 56" of the receiving part 5". Hence, when the first instrument part 1100 is attached to the receiving part 5" and the slits 1111 are aligned with the substantially U-shaped recess 53, the protrusions 56" can engage the recesses 1140 to fix the first instrument portion 1100 to the receiving part 5".

The instrument 1000 further includes a second instrument portion or inner member in the form of a pair of rod-shaped pushing members 1230a, 1230b housed in corresponding axially elongate compartments 1160 to the left and to the right of the recess 1140 in each of the arms 1120. Each pushing member 1230a, 1230b of one arm 1120 is configured to press onto one of the lever arms 75a, 75b of the actuating portion 7". The compartments 1160 may be open to the inside and to the outside of the arms 1120 in the radial direction, and the pushing members are guided in the compartments 1160. Moreover, the compartments 1160 are at a position such that the pushing members 1230a, 1230b are configured to press onto the respective lever arm 75a, 75b at a region close to the corresponding end portion 71a", 71b" of the bar 71", respectively. An end portion 1231 of each of the pushing members may have a convex outer surface to ensure contact with the lever surface 71c", 71d" in various pivot positions of the bar 71". Each pushing member 1230a, 1230b on each arm 1120 is movable in the axial direction from a first position in which the respective pushing member does not touch the bar 71" of the actuating portion 7" to a second position in which the end portion 1231 touches one of the lever arms 75a, 75b of the bar 71". In addition, each of the pushing members 1230a, 1230b is movable from the second position to the first position by the action of the other lever arm that pushes back the pushing member.

Figures 64, 65:
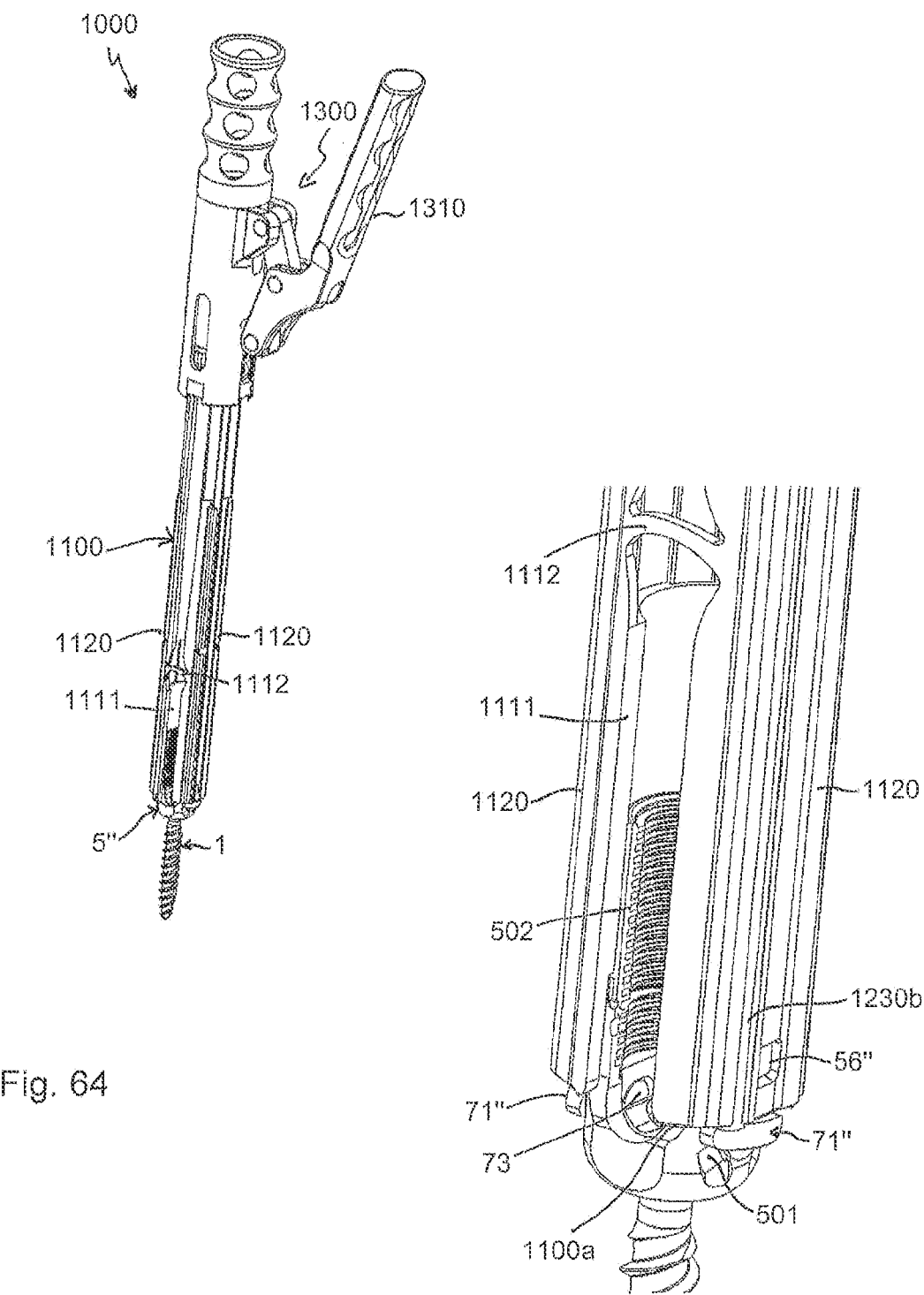
FIG. 64 shows a perspective view of an embodiment of an instrument for use with the polyaxial bone anchoring device of FIGS. 48 and 49.
FIG. 65 shows a perspective view of a portion of the instrument of FIG. 64 attached to the receiving part of the polyaxial bone anchoring device of FIGS. 48 and 49.
Figure 66:
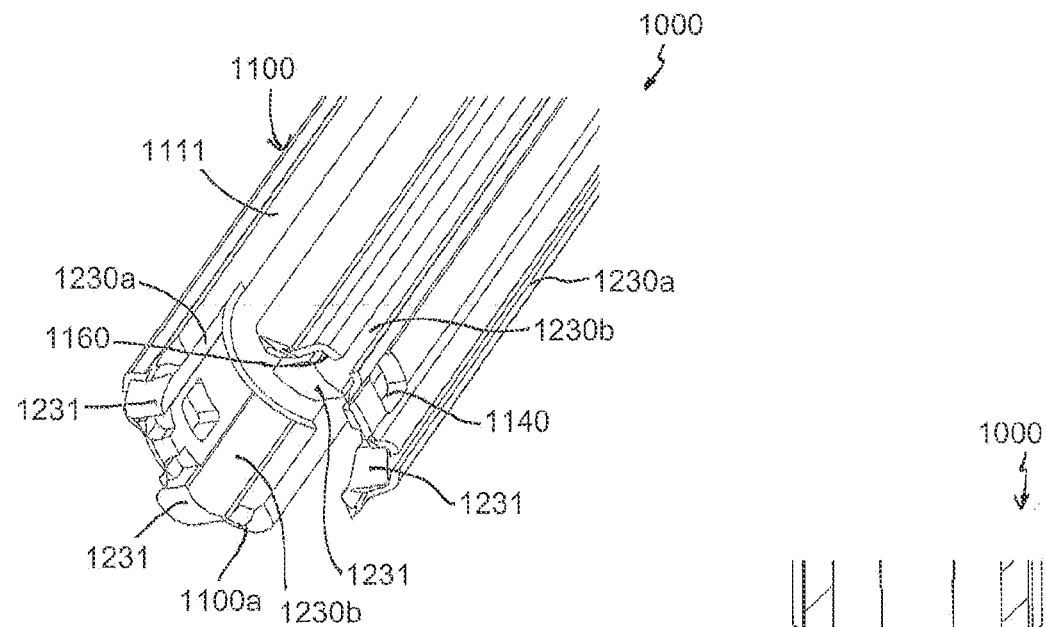
FIG. 66 shows a perspective view of a front portion of the instrument of FIGS. 64 and 65.
Figure 67:
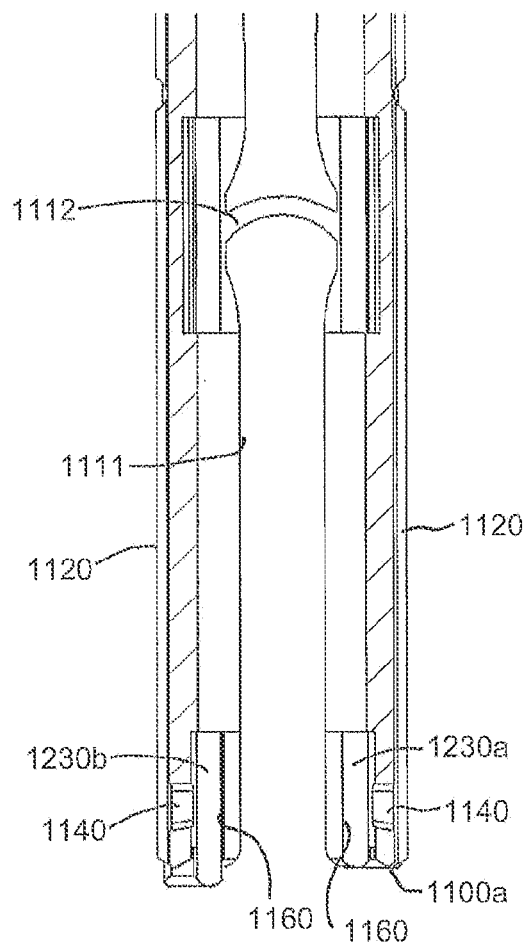
FIG. 67 shows a cross-sectional view of the front portion of the instrument of FIGS. 64 to 66.

As shown in FIG. 64, the instrument 1000 includes a mechanism 1300 for selectively actuating one of the pushing members 1230a, 1230b on each arm 1120 from the first position downward in the axial direction to press onto the lever arm 75a, 75b associated with that pushing member. At the same time, the other pushing member on the same arm is moved upward by the upward pressure exerted by the respective other lever arm. Specifically, the mechanism 1300 may include a lever 1310 which has two positions associated with the first and second positions of the pushing members.

Figure 68:
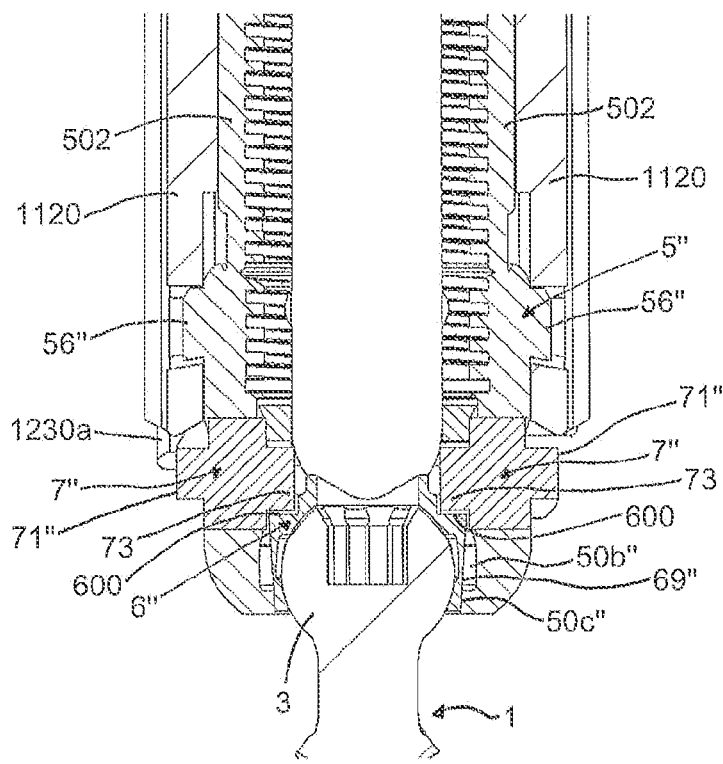
FIG. 68 shows a cross-sectional view of the polyaxial bone anchoring device of FIGS. 48 and 49 with a portion of the instrument of FIGS. 64 to 67 attached thereto, the cross-section taken in a plane including a central axis of the receiving part and extending through center of legs of the receiving part.

FIG. 68 shows the pressure member 6" in the locking position of the head 3, in which the conical outer surface 69" of the pressure member 6" engages the tapering inner surface 50c" of the receiving part 5", whereby the pressure member 6" is compressed around the head 3. The pushing member 1230a on the left side is pushed down and simultaneously the corresponding pushing member 1230a on the right side of the other arm (which is not shown in the cross-sectional view) is pushed down to press on the respective lever arms 75a. It shall be noted that due to the relatively small overlap of the conical outer surface 69" of the pressure member with the tapering inner surface 50c" of the receiving part 5", a relatively small force is needed for unlocking the device.

Figure 69A:
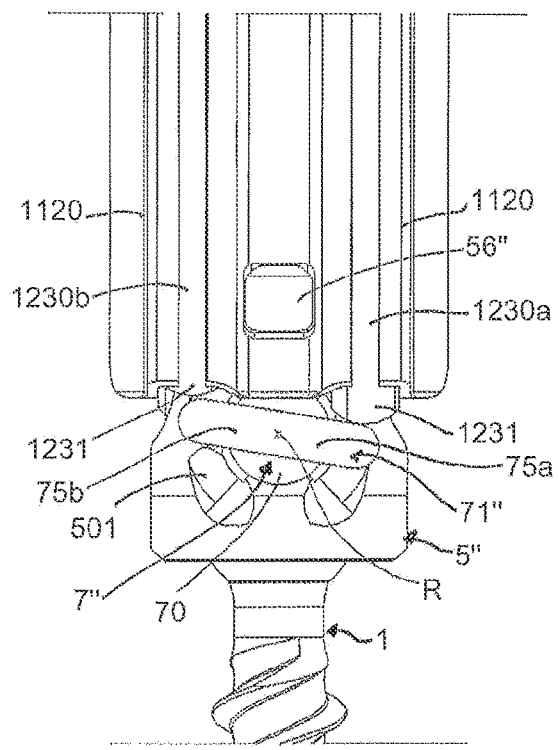
FIGS. 69a and 69b show side views of the instrument of FIGS. 64 to 67 attached to the polyaxial bone anchoring device of FIGS. 48 and 49, showing different configurations of the instrument and of the actuating portion of the receiving part, respectively.
Figure 69B:
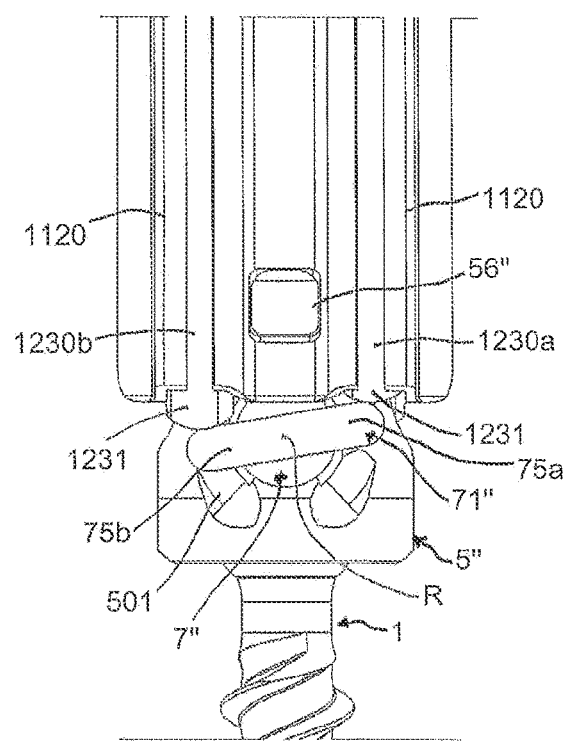

As shown in FIG. 69a, when one of the pushing members 1230a of one arm 1120 is pushed down to press on the corresponding lever arm 75a, the actuating portion 7" rotates in the clockwise direction and the eccentric protrusion 73 moves the pressure member 6" downward, i. e., towards the second end 5b of the receiving part, which results in locking of an inserted head. Thereby, the other one of the pushing members 1230b is moved upwards by the other lever arm 75b. As depicted in FIG. 69b, when the other one of the pushing members 1230b is moved downward, the pushing member 1230b presses on the other lever arm 75b to rotate the actuating member 7" in the counterclockwise direction, which results in moving the pressure member 6" upward. As a result, an inserted head can be unlocked. It shall be noted that, due to the inverted mounting of the other actuating portion 7" in the other hole 55" of the receiving part 5", the actuating portion provided on the other leg 54 of the receiving part 5" rotates in the opposite direction in each case.

Hence, the locking and unlocking can be associated with a specific configuration of the actuating mechanism 1300 of the instrument. Preferably, pressing the lever arm 1310 may be associated with locking of the head 3 and releasing the pressing of the lever arm 1310 may be associated with unlocking of the head. In use, the instrument can be snapped onto the receiving part until the protrusions 56" engage the corresponding recesses 1140 provided on the arm 1120. Thereafter, the pushing members can be actuated to lock an inserted head 3 and to unlock an inserted head 3. This procedure can be carried out several times.

Further modifications of the embodiments described are also possible. The features of one embodiment can also be combined with those of another embodiment to produce a variety of still further embodiments. The parts are not limited to their detailed shapes as depicted in the embodiments.

For example, the bone anchoring device is shown to be a bottom-loading bone anchoring device, where the head 3 is inserted from the second or lower end into the receiving part. The bone anchoring device in other embodiments may, however, be a top-loading bone anchoring device, where the bone anchor is inserted from the first end or top end into the receiving part. In such a case, the pressure member may have a slightly different design in that it covers the upper portion of the head and presses the head against a seat provided in the receiving part. In a further modification, only one actuating portion is present.

For the bone anchor, all kinds of bone anchors such as screws, nails, hooks, etc., may be used.

The mechanism for displacing the inner and outer member of the instruments may also be realized in various different manners.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling device for coupling a rod to a bone anchor, the coupling device comprising:
a receiving part configured to receive a head of the bone anchor, the receiving part having a first end and a second end, a central axis extending through the first end and the second end, two legs defining a recess at the first end for receiving the rod, and an accommodation space at the second end for accommodating the head;
a pressure member positionable in the receiving part, the pressure member comprising a head engaging surface movable along the central axis relative to the receiving part to adjust a pressure exerted on an inserted head; and
an actuating member separate from the receiving part and the pressure member that comprises an engagement surface configured to engage the pressure member;
wherein when a first portion of the actuating member moves axially in a first direction from a position closer to the first end of the receiving part to a position farther away from the first end of the receiving part, the engagement surface is configured to move from a first axial position to a second axial position relative to the receiving part to adjust the pressure member from a non-locking position where the head is pivotable relative to the receiving part to a locking position where an angular position of the head is locked relative to the receiving part; and
wherein when a second portion of the actuating member moves axially in the first direction, the engagement surface is configured to move from the second axial position back to the first axial position to adjust the pressure member from the locking position back to the non-locking position.

2. The coupling device of claim 1, wherein the actuating member is rotatable around an axis of rotation that is angled relative to the central axis to adjust the engagement surface between the first and second axial positions.

3. The coupling device of claim 1, wherein the actuating member is accessible laterally from outside the receiving part.

4. The coupling device of claim 1, wherein the actuating member comprises an insert configured to extend laterally through one of the two legs.

5. The coupling device of claim 1, wherein the engagement surface is arranged asymmetrically relative to a central axis of the actuating member.

6. The coupling device of claim 1, wherein the actuating member is secured to the receiving part by a stop.

7. The coupling device of claim 1, wherein the pressure member is movable axially relative to the receiving part between the non-locking position and the locking position.

8. The coupling device of claim 1, wherein the actuating member comprises an outer engagement portion that extends farther radially than an outer surface of the receiving part.

9. The coupling device of claim 1, wherein the actuating member is a first actuating member provided at one of the two legs, and wherein a second actuating member is provided at the other one of the two legs.

10. The coupling device of claim 1, wherein the receiving part further comprises an engagement portion on an outer surface of the receiving part that is engageable with an instrument.

11. The coupling device of claim 1, wherein the first portion of the actuating member comprises a first surface that is movable in the first direction to move the pressure member from the non-locking position to the locking position, and wherein the second portion of the actuating member comprises a second surface that is movable in the first direction to move the pressure member from the locking position back to the non-locking position.

12. The coupling device of claim 11, wherein the actuating member is configured to rotate in one direction when the first surface is moved in the first direction, and to rotate in the opposite direction when the second surface is moved in the first direction.

13. A bone anchoring device comprising the coupling device of claim 1 and a bone anchor comprising a head and a shank to be anchored in bone or in a vertebra.

14. The bone anchoring device of claim 13, wherein the receiving part defines an opening at the second end that is greater than a greatest width of the head to permit insertion of the head into the receiving part from the second end.

15. A coupling device for coupling a rod to a bone anchor, the coupling device comprising:
a receiving part configured to receive a head of the bone anchor, the receiving part having a first end and a second end, a central axis extending through the first end and the second end, and two legs defining a recess at the first end for receiving the rod;
a pressure member positionable in the receiving part, the pressure member comprising a head engaging surface configured to exert pressure on an inserted head; and
an actuating member separate from the receiving part and the pressure member and configured to extend laterally through one of the two legs while remaining completely spaced apart from the other one of the two legs, the actuating member comprising an engagement surface configured to engage the pressure member;
wherein when the engagement surface of the actuating member is at a first axial position located at a first distance from the first end of the receiving part, the pressure member is configured to assume a non-locking position in which the head is pivotable relative to the receiving part; and
wherein when the engagement surface is moved axially relative to the central axis from the first axial position to a second axial position located at a second distance from the first end of the receiving part that is different from the first distance, the pressure member is configured to move relative to the actuating member to a locking position in which an angular position of the head is locked relative to the receiving part.

16. The coupling device of claim 15, wherein the actuating member is rotatable around an axis of rotation that is angled relative to the central axis to adjust the engagement surface between the first and second axial positions.

17. The coupling device of claim 15, wherein the actuating member is secured in the one of the two legs by a stop.

18. The coupling device of claim 15, wherein the pressure member is movable along the central axis relative to the receiving part between the non-locking position and the locking position.

19. The coupling device of claim 15, wherein the actuating member comprises an outer engagement portion that extends farther radially than an outer surface of the receiving part.

20. The coupling device of claim 15, wherein the second axial position is farther away from the first end of the receiving part than the first axial position is to the first end of the receiving part.

21. A coupling device for coupling a rod to a bone anchor, the coupling device comprising:
- a receiving part configured to receive a head of the bone anchor, the receiving part having a first end and a second end, a central axis extending through the first end and the second end, two legs defining a recess at the first end for receiving the rod, and an accommodation space at the second end for accommodating the head;
- a pressure member positionable in the receiving part, the pressure member comprising a head engaging surface movable along the central axis relative to the receiving part to adjust a pressure exerted on an inserted head; and
- an actuating member separate from the receiving part and the pressure member that comprises an engagement surface configured to engage the pressure member;
- wherein the actuating member is rotatable around an axis of rotation that is angled relative to the central axis to move the engagement surface axially from a position closer to the first end of the receiving part to a position farther away from the first end of the receiving part for adjusting the pressure member from a non-locking position where the head is pivotable relative to the receiving part to a locking position where an angular position of the head is locked relative to the receiving part.

22. The coupling device of claim 21, wherein the actuating member comprises an insert that is rotatably supported in one of the two legs.

23. The coupling device of claim 21, wherein the engagement surface is arranged asymmetrically relative to the axis of rotation of the actuating member.

24. The coupling device of claim 23, wherein the pressure member defines a recess configured to receive the engagement surface of the actuating member, such that the engagement surface is movable in a guided manner in the recess to adjust the pressure member from the non-locking position to the locking position.

25. The coupling device of claim 21, wherein the pressure member is movable along the central axis relative to the receiving part from the non-locking position to the locking position.

26. The coupling device of claim 21, wherein the axis of rotation of the actuating member is perpendicular to the central axis.

27. The coupling device of claim 21, wherein the actuating member comprises an outer engagement portion that extends farther radially than an outer surface of the receiving part and that is asymmetric relative to the axis of rotation, such that applying a force in a direction parallel to the central axis on the outer engagement portion rotates the actuating member relative to the receiving part.

28. The coupling device of claim 21, wherein the actuating member is rotatable around the axis of rotation in a first direction to adjust the pressure member from the non-locking position to the locking position, and is rotatable around the axis of rotation in a direction opposite the first direction to adjust the pressure member from the locking position back to the non-locking position.

29. The coupling device of claim 21, wherein the actuating member is a first actuating member provided at one of the two legs, wherein a second actuating member is provided at the other one of the two legs, and wherein the two actuating members are configured to rotate in opposite directions from one another to adjust the pressure member from the non-locking position to the locking position.

* * * * *